United States Patent
Ackerman et al.

(10) Patent No.: US 11,167,012 B2
(45) Date of Patent: Nov. 9, 2021

(54) PEPTIDE INHIBITION OF CCR3-MEDIATED DISEASES OR CONDITIONS

(71) Applicants: The Board of Trustees of the University of Illinois, Urbana, IL (US); The USA, as represented by the Secretary, Department of Health and Human Services, Bethesda, MD (US)

(72) Inventors: Steven Jules Ackerman, Naperville, IL (US); Fan Gao Laffey, Chicago, IL (US); Ben Hitchinson, Chicago, IL (US); Boris Garnier, Chatanay-malabry (FR); Vadim Gaponenko, Naperville, IL (US); Nadya Tarasova, Frederick, MD (US); Hazem Abdelkarim, Worth, IL (US)

(73) Assignees: The Board of Trustees of the University of Illinois, Urbana, IL (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 91 days.

(21) Appl. No.: 16/525,056

(22) Filed: Jul. 29, 2019

(65) Prior Publication Data
US 2019/0374608 A1 Dec. 12, 2019

Related U.S. Application Data

(60) Division of application No. 15/639,434, filed on Jun. 30, 2017, now Pat. No. 10,363,286, which is a continuation-in-part of application No. PCT/US2016/017714, filed on Feb. 12, 2016.

(60) Provisional application No. 62/115,880, filed on Feb. 13, 2015.

(51) Int. Cl.
| | |
|---|---|
| A61K 38/19 | (2006.01) |
| C07K 14/715 | (2006.01) |
| C07K 14/47 | (2006.01) |
| A61P 37/08 | (2006.01) |
| A61P 11/06 | (2006.01) |
| A61K 47/68 | (2017.01) |
| A61K 47/10 | (2017.01) |
| C07K 14/52 | (2006.01) |
| A61K 38/00 | (2006.01) |
| A61K 9/00 | (2006.01) |

(52) U.S. Cl.
CPC ............ *A61K 38/195* (2013.01); *A61K 47/10* (2013.01); *A61K 47/6813* (2017.08); *A61P 11/06* (2018.01); *A61P 37/08* (2018.01); *C07K 14/4703* (2013.01); *C07K 14/521* (2013.01); *C07K 14/7158* (2013.01); *A61K 9/008* (2013.01); *A61K 38/00* (2013.01)

(58) Field of Classification Search
CPC ........ A61P 37/08; A61P 11/06; C07K 14/521; C07K 14/4703; C07K 14/7158; A61K 47/6813; A61K 38/195; A61K 9/008; A61K 38/00; A61K 47/10
See application file for complete search history.

(56) References Cited

U.S. PATENT DOCUMENTS

| | | | |
|---|---|---|---|
| 7,105,488 B1 | 9/2006 | Tarasova | |
| 2003/0229121 A1* | 12/2003 | Du Bois | ............ C07D 295/135 514/317 |
| 2010/0143268 A1 | 6/2010 | Kellaway | |
| 2013/0156723 A1 | 6/2013 | Gonzalez | |

FOREIGN PATENT DOCUMENTS

| | | |
|---|---|---|
| WO | 1999043711 A1 | 9/1999 |
| WO | 2000073327 A1 | 12/2000 |
| WO | 2007105224 A1 | 9/2007 |
| WO | 2010149964 A2 | 12/2010 |

OTHER PUBLICATIONS

Asthma, from https://www.mayoclinic.org/diseases-conditions/asthma/symptoms-causes/syc-20369653? . . . , pp. 1-5, accessed Mar. 29, 2021.*
Asthma-Pulmonary Disorders—Merck Manuals Professional Edition, from https://www.merckmanuals.com/professional/pulmonary-disorders/asthma-and-related-disorders/asthma?query=asthma#, pp. 1-13, accessed Mar. 29, 2021.*
Pease et al, Recent progress in the development of antagonists to the chemokine receptors CCR3 and CCR4, Expert Opin. Drug Discov., 2014, 9, pp. 467-483.*
Korbecki et al, CC Chemokines in a Tumor: A Review of Pro-Cancer and Anti-Cancer Properties of the Ligands of Receptors CCR1, CCR2, CCR3, and CCR4, Int. J. Mol. Sci., 2020, 21, pp. 1-29.*
Veronese et al, PEGylation, successful approach to drug delivery, DDT, 2005, 10, pp. 1451-1458.*
Bertrand et al, CCR3 blockade as a new therapy for asthma, Exp. Opin. Invest. Drugs, 2000, 9, pp. 43-52.*

(Continued)

*Primary Examiner* — Li N Komatsu

(74) *Attorney, Agent, or Firm* — Licata & Tyrrell P.C.

(57) ABSTRACT

A C—C chemokine receptor 3 (CCR3) peptide analog that exhibits biased antagonism by binding to and inhibiting ligand-mediated signaling and chemotaxis while promoting the internalization and degradation of CCR3 is provided as is a method of using the peptide analog to treat, prevent, or ameliorate one or more symptoms of an eosinophil- or CCR3-mediated disease or condition.

3 Claims, 9 Drawing Sheets
Specification includes a Sequence Listing.

(56) References Cited

OTHER PUBLICATIONS

Gonzalez-Rothi et al, Pulmonary Delivery of Liposome-Encapsulated Drugs in Asthma Therapy, Clin. Immunother., 1995, 4, pp. 331-337.*
Fulkerson et al. (2006) "A central regulatory role for eosinophils and the eotaxin/CCR3 axis in chronic experimental allergic airway inflammation." Proceedings of the National Academy of Sciences USA. 103(44):116418-23.
Laffey et al. (2015) "Development of a Novel Peptide Nanoparticle Inhibitor for Human CCR3/Eotaxin-Mediated Eosinophil Migration" Journal of Allergy and Clinical Immunology. 135(2), Supplement S:AB160.
Ying et al. (1997) "Enhanced expression of eotaxin and CCR3 mRNA and protein in atopic asthma. Association with airway hyperresponsiveness and predominant co-localization of eotaxin mRNA to bronchial epithelial and endothelial cells." European Journal of Immunology. 27(12):13507-3516.
International Search Report and Written Opinion in PCT/US2015/064202 dated Feb. 11, 2016.
Supplemental Partial Search Report dated Jul. 2, 2018 in EP 16749945 filed Feb. 12, 2016.
Office Communication dated Jul. 17, 2018 from U.S. Appl. No. 15/639,434, filed Jun. 30, 2017.
Office Communication dated Nov. 20, 2018 from U.S. Appl. No. 15/639,434, filed Jun. 30, 2017.

\* cited by examiner

✕ HARVEST BLOOD, BAL, LUNG TISSUE

PEPTIDE INHIBITION OF CCR3-MEDIATED DISEASES OR CONDITIONS

This application is a divisional of U.S. Ser. No. 15/639,434 filed Jun. 30, 2017, now U.S. Pat. No. 10,363,286 B2, which is a continuation-in-part application of PCT/US2016/017714, filed Feb. 12, 2016, which claims benefit of priority to U.S. Provisional Patent Application Ser. No. 62/115,880, filed Feb. 13, 2015, the content of which is incorporated herein by reference in its entirety.

This invention was made with government support under contract number R21HL118588 awarded by the National Institutes of Health. The government has certain rights in the invention.

BACKGROUND

In allergic disorders such as asthma and eosinophilic esophagitis (EoE), eosinophils are recruited into the lung and esophagus respectively, and activated in excess at these sites of inflammation. Eosinophils are implicated as one of the major effector cell types contributing to the pathology of these diseases. Signaling through C—C chemokine receptor 3 (CCR3), a G-protein coupled receptor (GPCR), is a critical process responsible for eosinophil recruitment.

While CCR3 is most highly expressed by eosinophils, it is also expressed by basophils, and subsets of mast cells and Th2 cells. It can be activated by a variety of chemokines including, but not limited to, the eotaxins (CCL11, CCL24, CCL26), RANTES (CCL5), MEC (CCL28), MCP-3 and MCP-4. The activation and desensitization triggered by ligand binding has not been exhaustively investigated for CCR3. However, CCR3 activation by the eotaxins and RANTES has been shown to result in calcium mobilization, activation of the MAPK/ERK1/2 and MAPK/p38 pathways, and activation of the PI3K/AKT pathway. Activation of these intracellular signaling pathways culminates in the priming, chemotaxis, activation and degranulation of the eosinophil. Concurrently, CCR3 is internalized and at least partially degraded. Eotaxin-induced CCR3 internalization has also been shown to be required for actin polymerization and chemotaxis.

The importance of CCR3 as a potential therapeutic target has been established through the observations that CCR3-null mice and eotaxin-1 and -2 double knockout mice display near complete abolishment of allergen-induced eosinophil recruitment to the airways (Fulkerson, et al. (2006) *Proc. Natl. Acad. Sci. USA* 103:16418-16423). There is also increased CCR3 transcript and protein levels in the bronchial mucosa of patients with allergic asthma (Ying, et al. (1997) *Eur. J. Immunol.* 27:3507-3516). In line with this, efforts have been made to develop small molecule CCR3 antagonists. For example, small molecule competitive inhibitors of CCR3 such as UCB35625 (1,4-trans-1-(1-Cycloocten-1-ylmethyl)-4-[[(2,7-dichloro-9H-xanthen-9-yl)carbonyl]amino]-1-ethylpiperidinium iodide), GW766994 (1-(4-acetyl-benzyl)-3-[4-(3,4-dichloro-benzyl)-morpholin-2-ylmethyl]-urea) and SB328437 (N-(1-Naphthalenylcarbonyl)-4-nitro-L-phenylalanine methyl ester) have been described. However, such molecules are typically unbiased antagonists that inhibit both chemotaxis and receptor internalization (endocytosis), leading to receptor accumulation on the cell surface. As a result, such antagonists lose their potency after prolonged administration, a phenomenon commonly referred to as drug tolerance.

Further, WO 1999/043711 and U.S. Pat. No. 7,105,488 describe monomeric CCR3 transmembrane peptides such as LLFLVTLPFWIHYVRGHNWVFGDDD (SEQ ID NO:1), FGVITSIVTWGLAVLAALPEFIFYETED (SEQ ID NO:2), IFVXMAVFFIFWTPYNVAILLSSYQSDD (SEQ ID NO:3, X=T or I), and DDLVMLVTEVIAYSHCCMNPVIYAFV (SEQ ID NO:4), which insert into a membrane in the same orientation as the transmembrane domain from which it is derived, and modulate GPCR biological activity. Peptide derivatives such as post-translational modifications and the addition of charged residues to the peptide termini are suggested to improve solubility, whereas the generation of peptidomimetics is described for increasing resistance to degradation by proteolytic enzymes.

SUMMARY OF THE INVENTION

This invention is a C—C chemokine receptor 3 (CCR3) peptide analog having the amino acid sequence $Xaa_1$-Leu-Phe-Leu-$Xaa_2$-Thr-$Xaa_3$-$Xaa_4$-Phe-Trp-Ile-His-Tyr (SEQ ID NO:15), wherein $Xaa_1$ denotes Val or Leu, $Xaa_2$ denotes Phe or Val, $Xaa_3$ denotes Leu or Val, and $Xaa_4$ denotes Pro or Val, and said peptide analog is PEGylated. In some embodiments, the peptide analog is up to 30 or 50 amino acid residues in length. In other embodiments, the peptide analog has the amino acid sequence LLNLAISDLL-FLVTLPFWIHYDDDC (SEQ ID NO:19) or LLFLVTLPFWIHYVRGHNWVFGHDDD (SEQ ID NO:20). In further embodiments, the PEGylated peptide has between 5 and 50 PEG units. In particular embodiments, the CCR3 peptide analog is LLFLVTLPFWIHYVRGHNWVFGHDDD-$PEG_{27}$-$NH_2$ (SEQ ID NO:21). A nanoparticle composition containing the CCR3 peptide analog is also provided as is a pharmaceutical composition and metered dose inhaler containing the same. In certain embodiments, the nanoparticle composition further includes a second therapeutic agent.

This invention is also a method for treating, preventing, or ameliorating one or more symptoms of an eosinophil- or CCR3-mediated disease or condition in a subject by administering to the subject an effective amount of a pharmaceutical composition containing the CCR3 peptide analog or nanoparticle thereof. In some embodiments the composition is administered to the lungs of the subject, e.g., via nebulization. In other embodiments, the composition is administered to the esophagus, e.g., via an oral viscous preparation that coats the esophagus.

UCB35625, non-selective CCR3 inhibitor. Error bars show SEM. *p<0.05, compared to uninhibited chemokine-induced cells; n≥3.

Figure 4A:
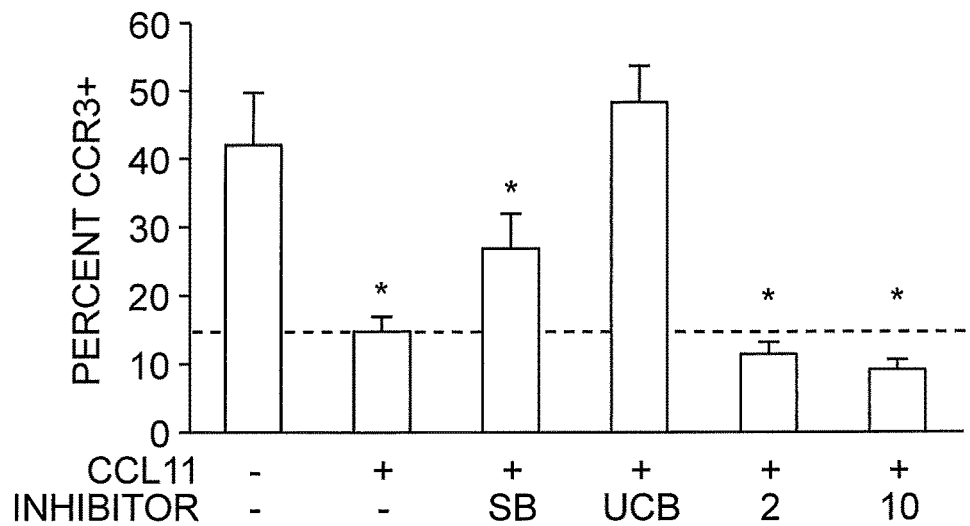
Figure 4B:
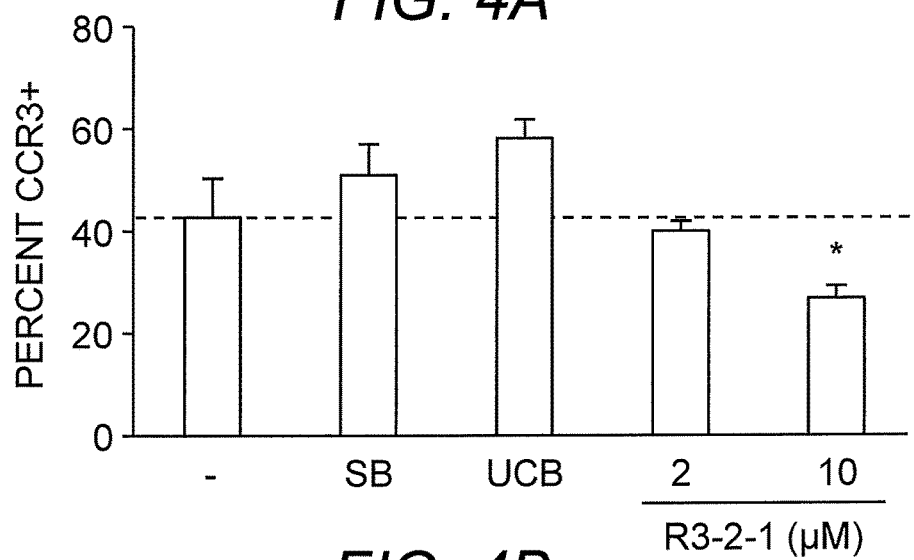
Figure 4C:
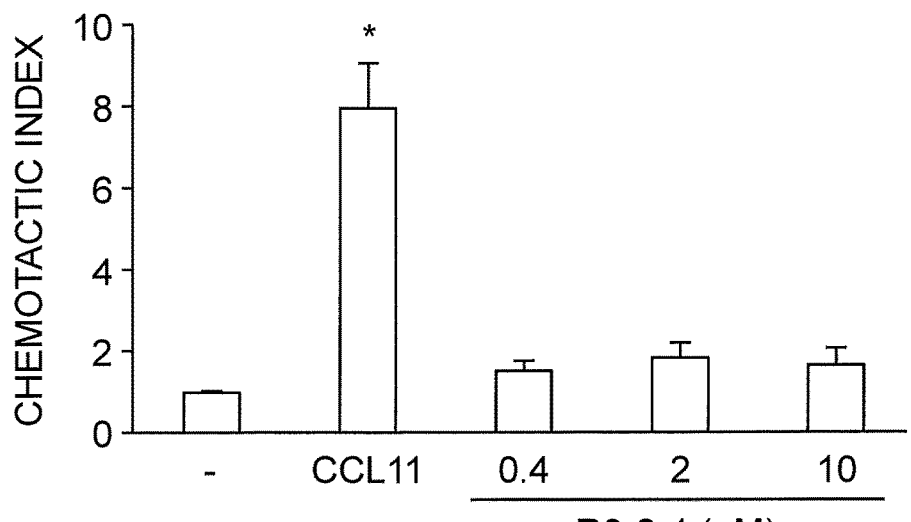

FIG. 4A to FIG. 4C show that R3-2-1 exerts its inhibitory effect in part by down-regulating surface CCR3. As shown in FIG. 4A, R3-2-1 (2 or 10 μM) does not inhibit CCL11-induced CCR3 endocytosis compared to CCR3 antagonists SB328437 (SB; 10 μM) and UCB35625 (UCB; 10 μM). Further, in the absence of CCR3 ligand, only R3-2-1 significantly decreases surface CCR3 expression in AML14.3D10-CCR3 cells as quantified by flow cytometry (FIG. 4B). Despite being able to induce CCR3 internalization, R3-2-1 by itself is not chemotactic for AML14.3D10-CCR3 cells (FIG. 4C). Error bars represent SEM. *p<0.05, compared to untreated cells; n=3.

Figure 5A:
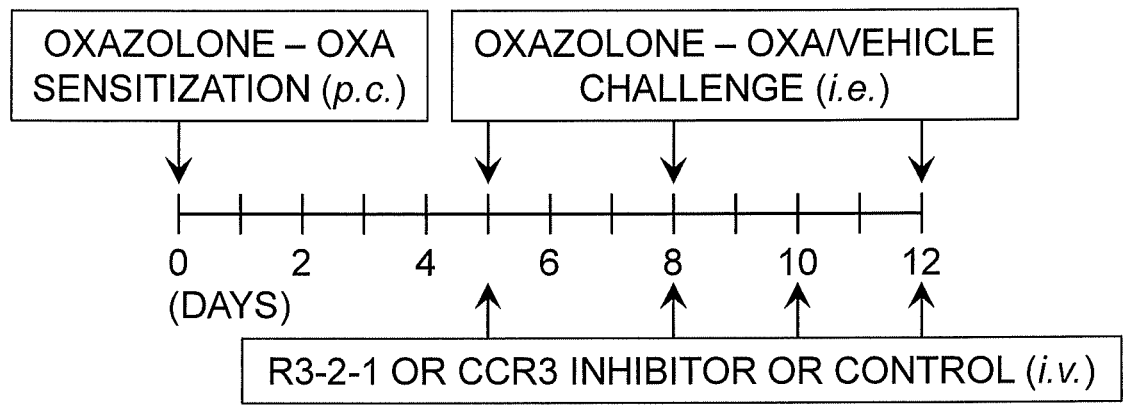
Figure 5B:
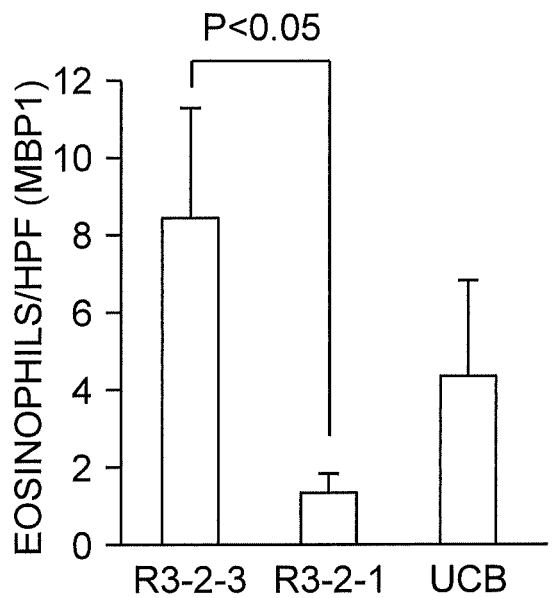
Figure 5C:
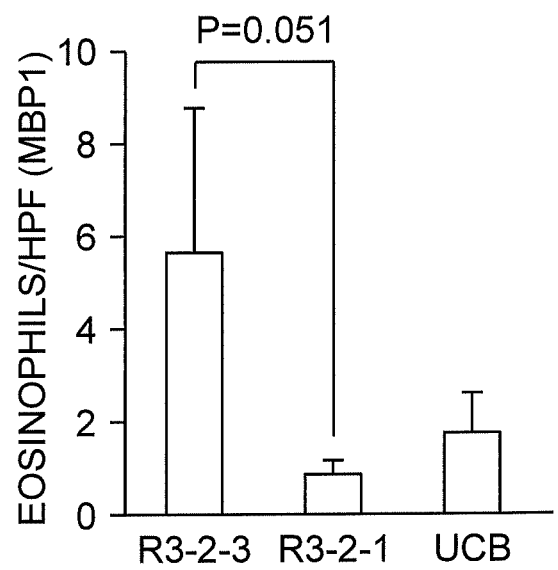

FIG. 5A to FIG. 5C show that R3-2-1 blocks eosinophil recruitment into the esophagus in a mouse model of EoE. Skin sensitized L2-IL5 transgenic mice received topical esophageal oxazalone (OXA) challenges by gavage (i.e.) on days 5, 8 and 12 (FIG. 5A). R3-2-1 peptide nanoparticles, control peptide (R3-2-3) or CCR3 inhibitor UCB35625 (UCB) were given immediately before on days 5, 8, 10 and 12 (FIG. 5A). Esophageal eosinophilia was assessed 24 hours after the last OXA challenge and treatment (day 13). R3-2-1 significantly blocked eosinophil recruitment into the distal esophageal epithelium (FIG. 5B) and total esophageal epithelium, while UCB35625 had no effect (FIG. 5C). Error bars represent SEM.

Figure 6A:
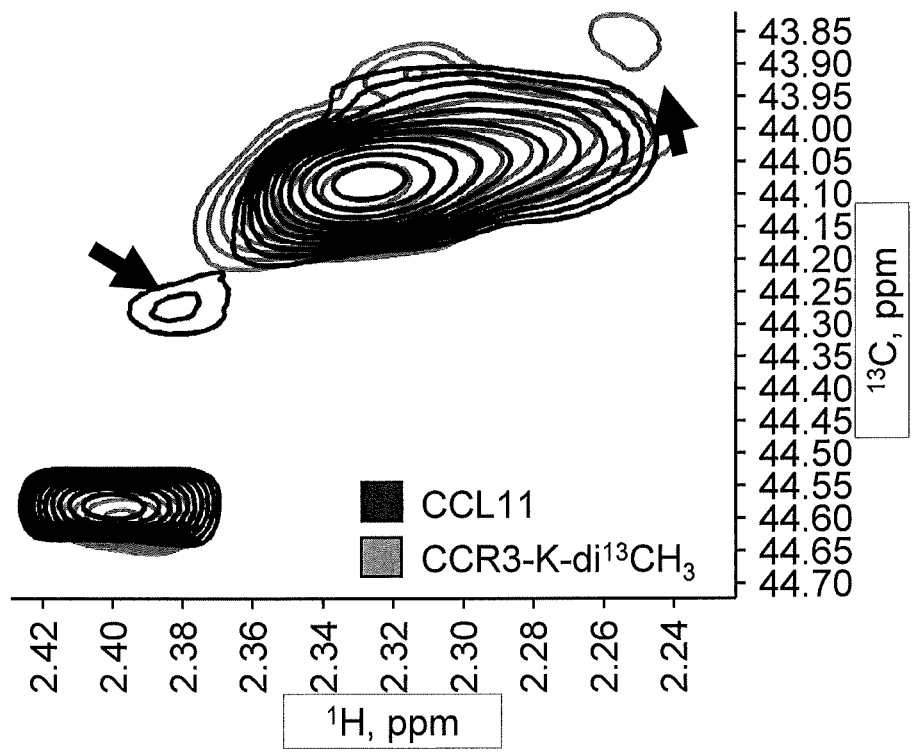
Figure 6B:
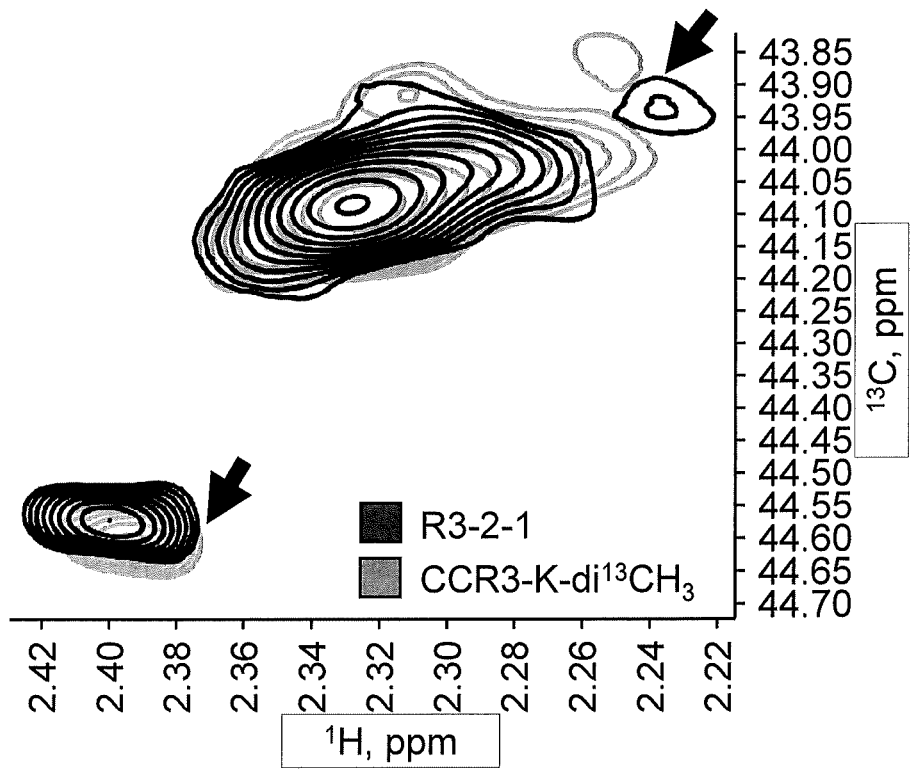
Figure 6C:
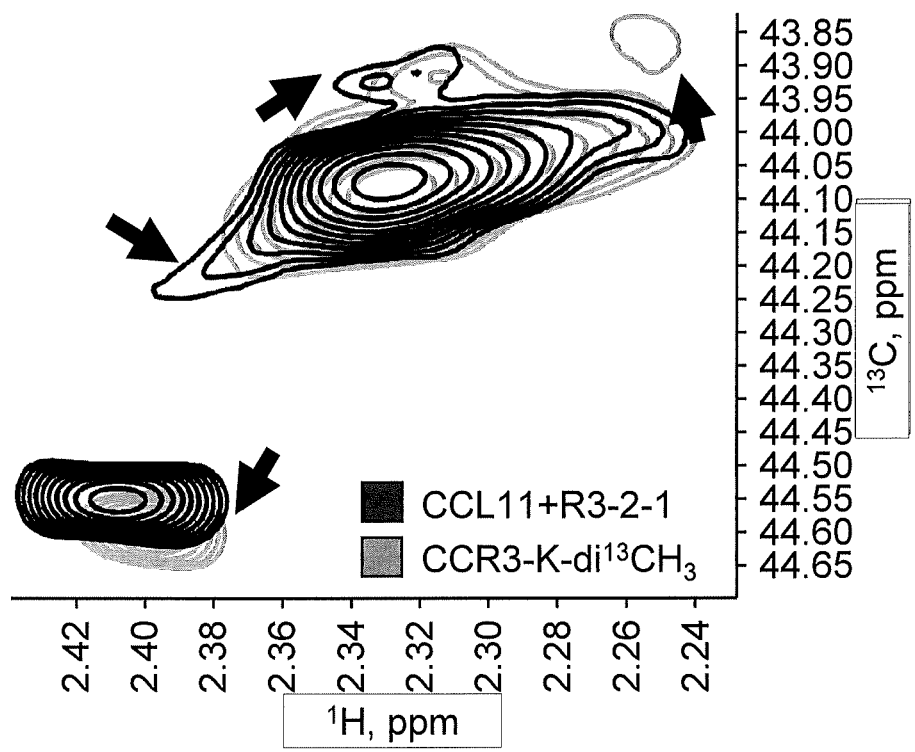
Figure 6D:
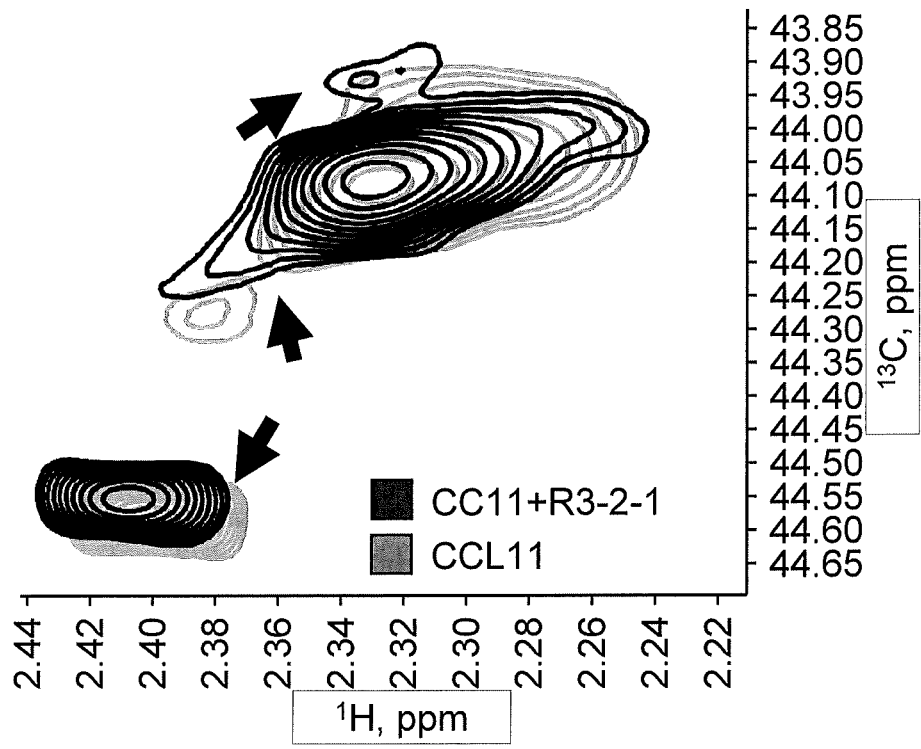
Figure 6E:
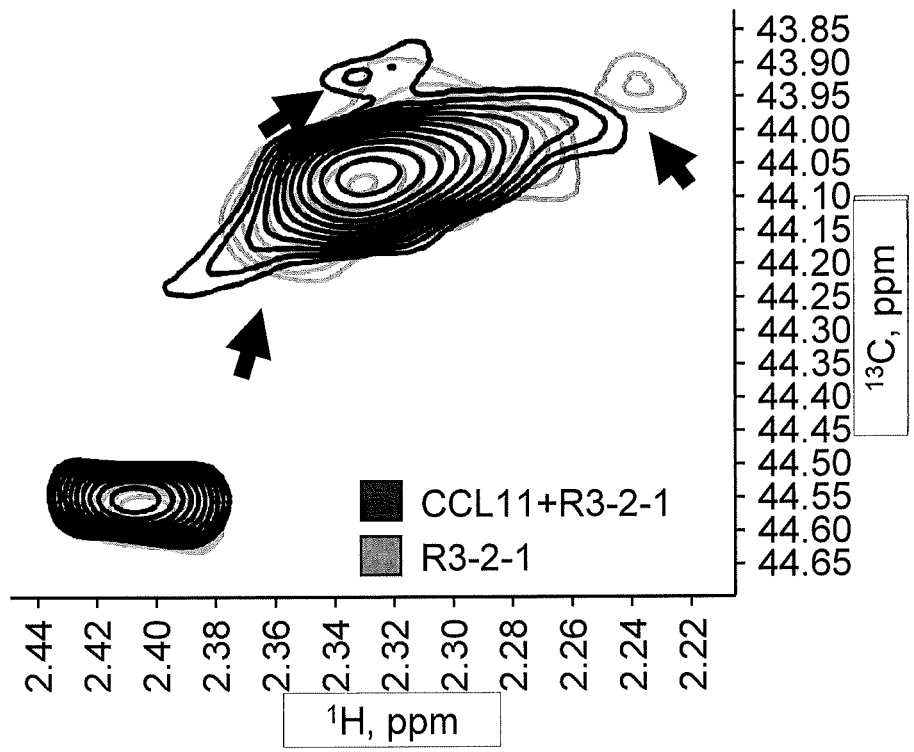

FIG. 6A to FIG. 6E show NMR evaluation of the binding of R3-2-1 and CCL11/eotaxin-1 to CCR3 membrane preparations. $^{13}C$ HSQC spectra of $^{13}C$-reductively methylated CCR3 membrane preps (0.25 mg/ml) were recorded with 1 μM CCL11 and 10 μM R321. FIG. 6A, reductively methylated CCR3 (CCR3-K-di$^{13}$CH3) (gray) and reductively methylated CCR3 with CCL11 (black); FIG. 6B, reductively methylated CCR3 (CCR3-K-di$^{13}$CH3) (gray) and reductively methylated CCR3 with R321 (black); FIG. 6C, reductively methylated CCR3 (CCR3-K-di$^{13}$CH3) (gray) and reductively methylated CCR3 with CCL11 and R321 (black); FIG. 6D, reductively methylated CCR3 with CCL11 (gray) and reductively methylated CCR3 with CCL11 and R321 (black); and FIG. 6E, reductively methylated CCR3 with R321 (gray) and reductively methylated CCR3 with CCL11 and R321 (black) show chemical shift changes indicative of binding. Black arrows indicate the differences in chemical shifts.

Figure 7:
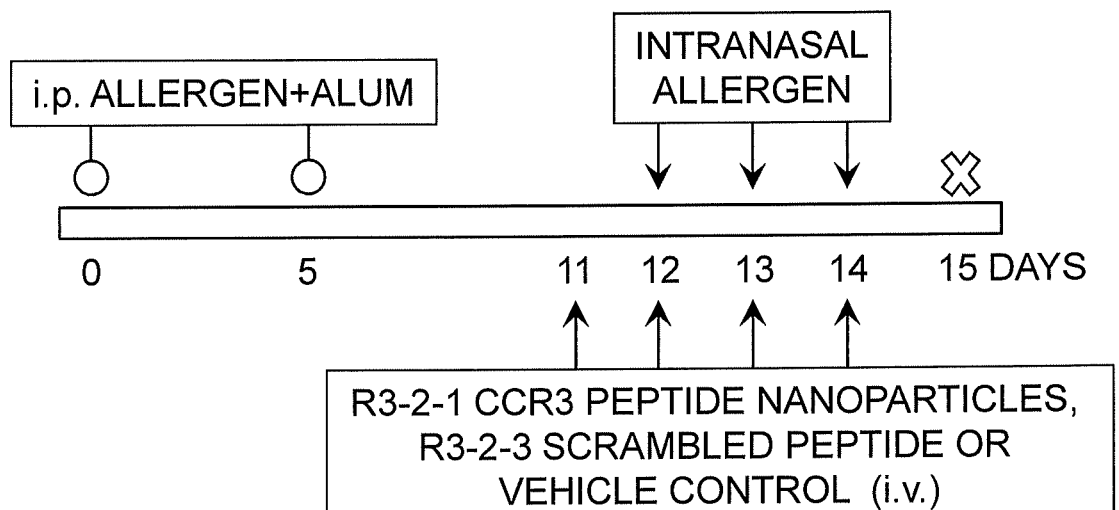

FIG. 7 shows the triple antigen (Dust mite, Ragweed, *Aspergillus*, DRA) allergic mouse asthma model protocol in sensitized and challenged wild-type C57BL6 or Balb/c mice. Treatment of mice with CCR3 R3-2-1 peptide nanoparticles, scrambled R3-2-3 peptide nanoparticles or vehicle controls was administered i.v. by retro-orbital injection starting on day 11, one day before intranasal DRA allergen challenges on days 12-14 to assess its effect on inhibiting the recruitment of eosinophils into the lung airspaces and airways. Blood, bronchoalveolar lavage (BAL) fluid and lung tissue were harvested on day 15.

Figure 8:
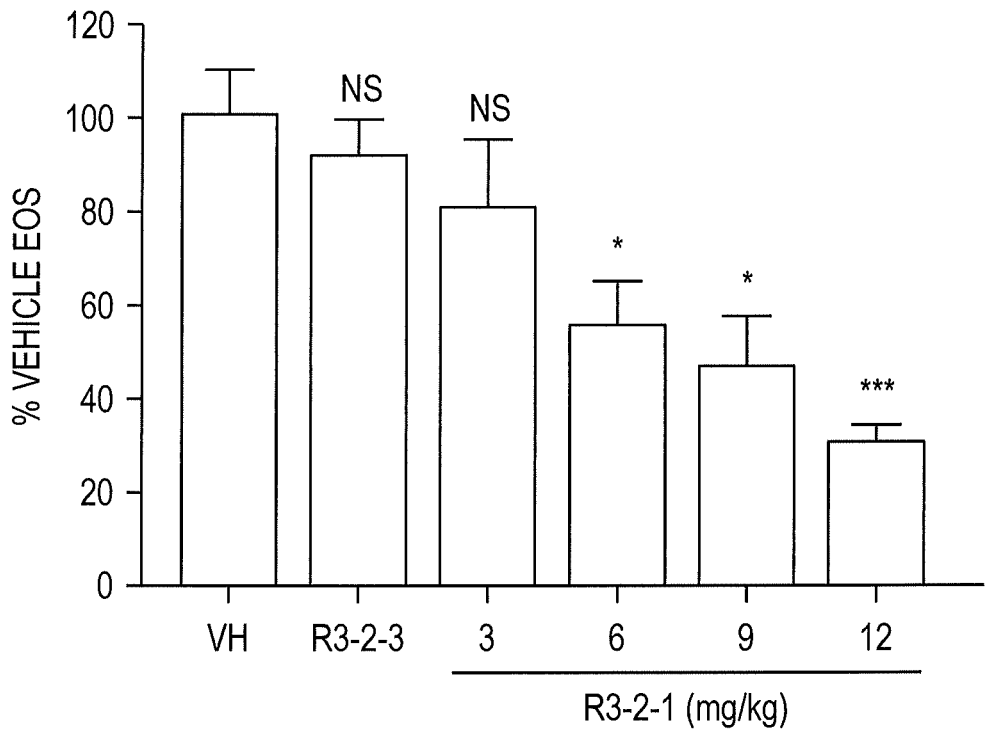

FIG. 8 shows that the inhibitory effect of R3-2-1 administered i.v. on eosinophil (EOS) recruitment (eosinophil counts in bronchoalveolar lavage [BAL] fluid as a % of the vehicle control) is dose-dependent with a maximum 69.3% reduction in mice treated with 12 mg/kg R3-2-compared to vehicle (Vh) and R3-2-3 scrambled peptide controls. The mean±SEM are shown for 6-7 mice/treatment group combined from 3 independent experiments (***p<0.001, *p<0.05, $^{ns}$ not significant).

Figure 9:
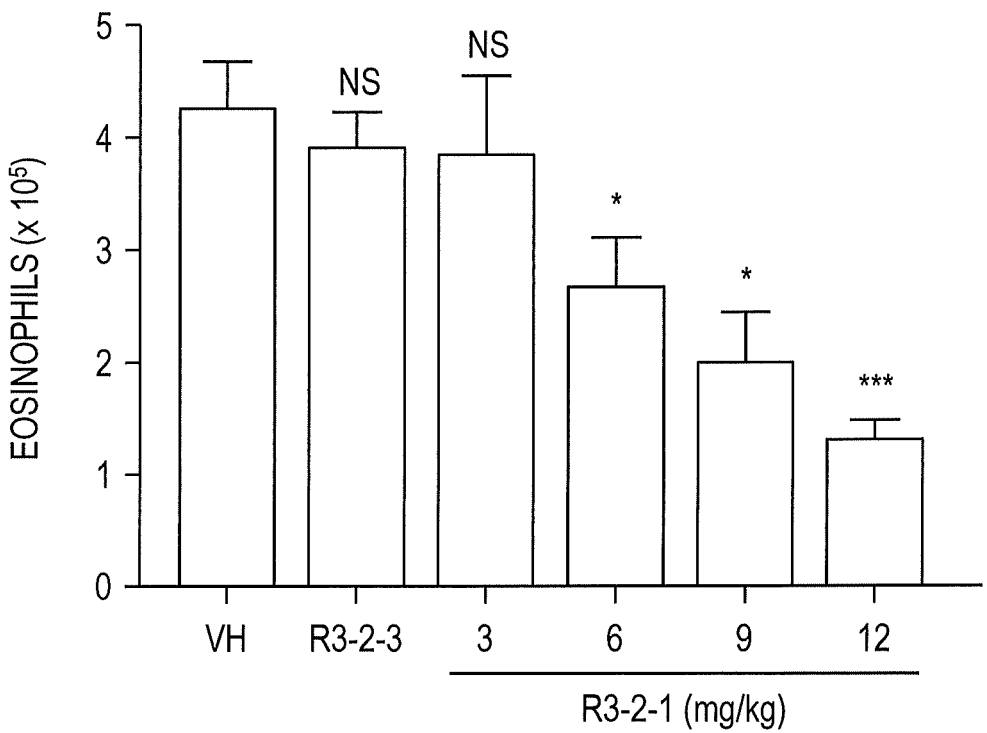

FIG. 9 shows the total eosinophil cell numbers ($\times 10^5$) in the BAL fluid from the analysis in FIG. 8. The results show that R3-2-1 significantly inhibits the total number of eosinophils recruited into the lung airspaces in a dose-dependent manner. The mean±SEM are shown for 6-7 mice/treatment group combined from 3 independent experiments (***p<0.001, *p<0.05, $^{ns}$ not significant).

Figure 10:
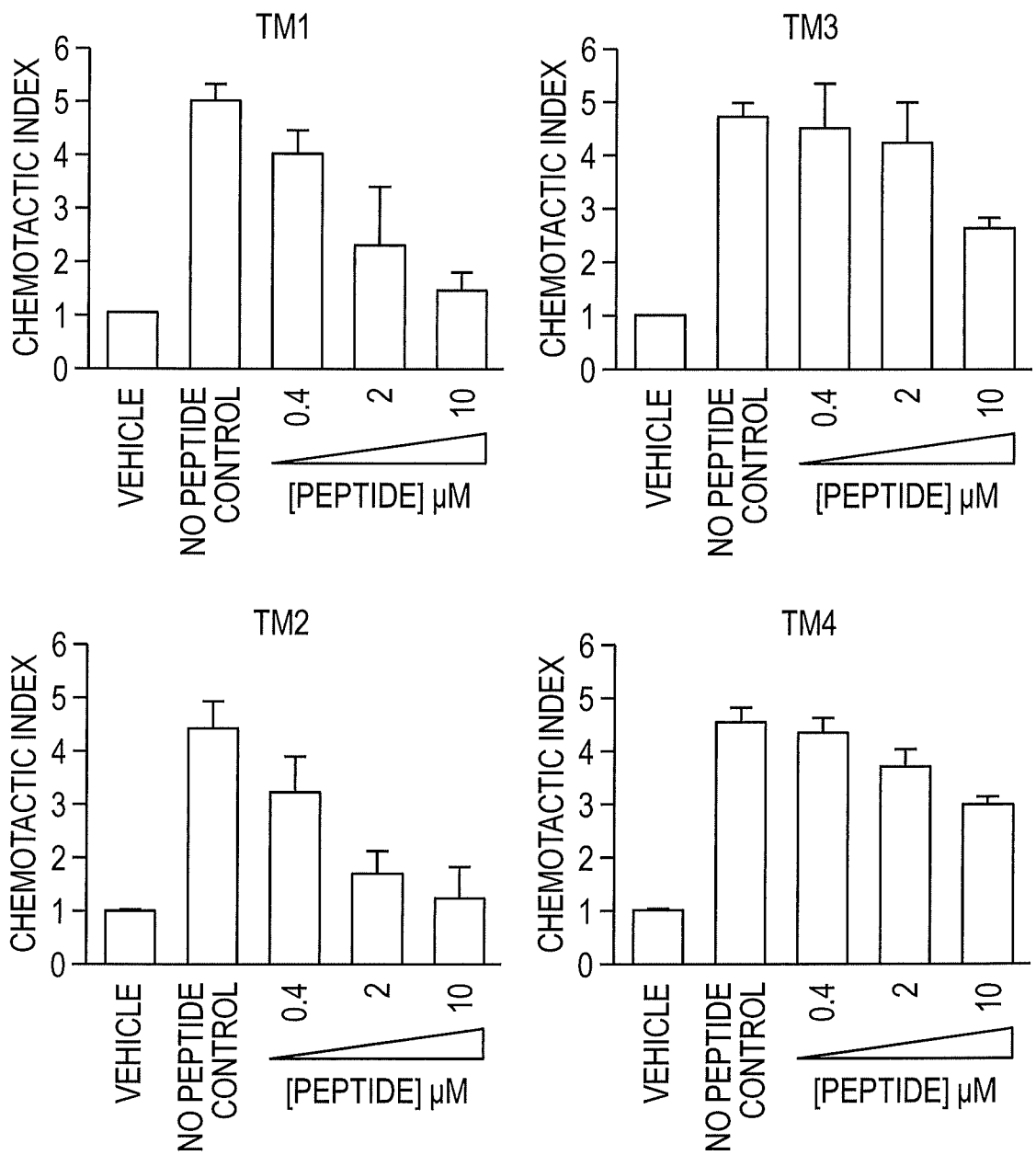

FIG. 10 shows the effects of linear peptides derived from CCR3 transmembrane domains on eotaxin-induced chemotaxis of 4DE4-CCR3 cells. Cells were pretreated with, and then allowed to migrate towards, 80 nM eotaxin in the presence of the various CCR3 transmembrane peptides for 4 hours. Data are from three independent experiments. Error bars represent SEM.

DETAILED DESCRIPTION OF THE INVENTION

Many small molecule CCR3 antagonists such as UCB35625 are characterized to be full antagonists (Sabroe, et al. (2000) *J. Biol. Chem.* 275:25985). That is, they act to inhibit both the activation branch as well as the desensitization and degradation branch of CCR3 signaling following ligand binding. In this scenario, the cell increases in surface receptor density as the basal turnover process continues to produce new receptors. Receptor accumulation likely explains the limited in vivo success observed with such antagonists (Neighbour, et al. (2014) *Clin. Exp. Allergy* 44: 508-516) as eosinophils eventually overcome inhibition and become resistant.

Figure 1:
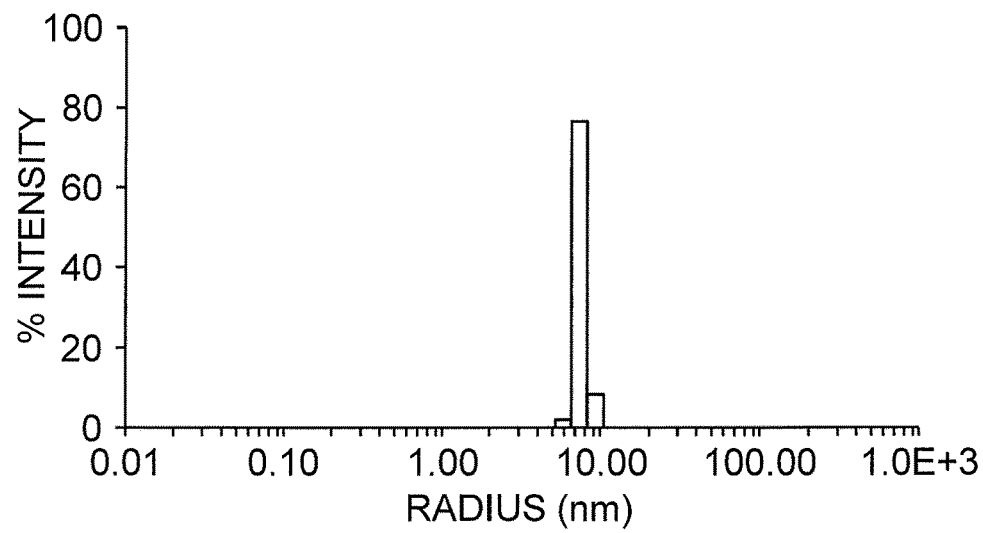
FIG. 1 shows a dynamic light scattering regularization distribution histogram for a 0.4 mg/ml R-3-2-1 peptide solution in phosphate-buffered saline (PBS).
Figure 2A:
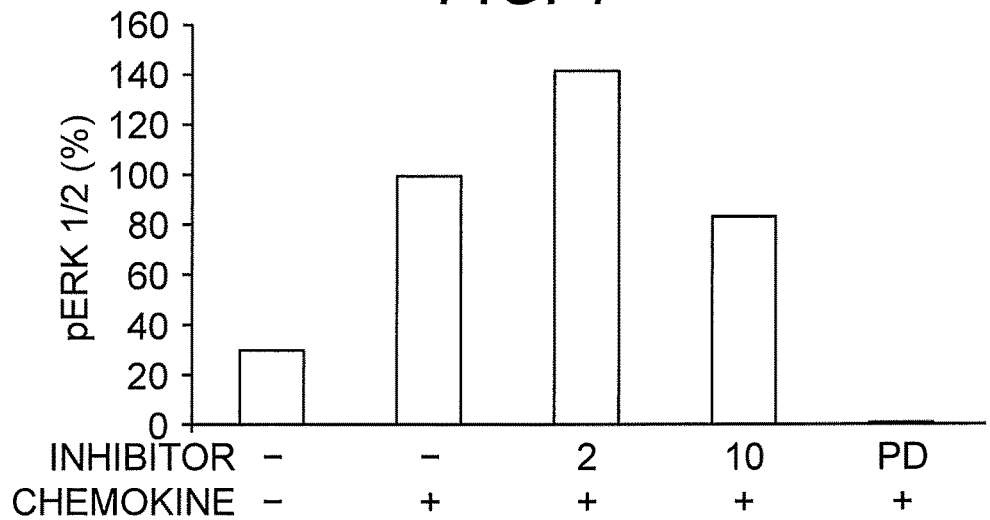
FIG. 2A and FIG. 2B show that R3-2-1 (2 and 10 µM) inhibits activation of the MAPK pathway by RANTES (FIG. 2A) and eotaxin (FIG. 2B) as shown by inhibition of ERK1/2 phosphorylation. Phospho-ERK was detected using a specific antibody. The membrane was stripped and reprobed for total ERK1/2 as loading control. Immunoblots were quantified by densitometry using ImageJ. PD: PD184161, MEK inhibitor.
Figure 2B:
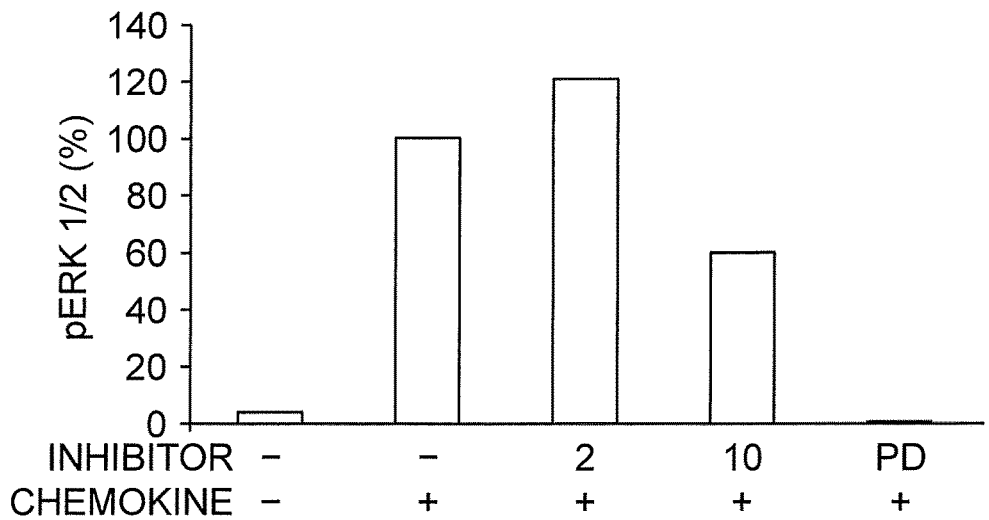

It has now been shown that a peptide analog of the CCR3 second transmembrane helix, referred to herein as R3-2-1, exhibits biased antagonism by binding and promoting the internalization (endocytosis) and degradation of CCR3 while at the same time inhibiting CCR3-mediated signaling and chemotaxis. Of significance, the R3-2-1 peptide analog auto-assembles in aqueous medium into uniform size nanoparticles (FIG. 1), thereby protecting the peptide from proteolytic degradation in blood and other body fluids, and inhibits CCR3 signal transduction including activation of Gαi and phosphorylation of ERK1/2 in response to eotaxin or RANTES stimulation (FIG. 2A and FIG. 2B). Further, the R3-2-1 peptide analog attenuates CCR3-mediated chemotaxis in vitro (FIG. 3) and in vivo (FIG. 5A to FIG. 5C). Accordingly, the present invention provides the CCR3 peptide analog, as well as compositions and methods of using the peptide analog to inhibit CCR3 activity and treat disease.

For the purposes of this invention, a "peptide" refers generally to a single linear chain of amino acid residues joined together through amide bonds. All of the amino acids used in the present invention may be either the D- or L-isomer. In some embodiments, the peptide analog of the invention has an amino acid sequence of less than 50, 40, or 30 amino acid residues. In other embodiments, a peptide analog of the invention has between 13 and 50, 13 and 40, or 13 and 30 amino acid residues. In particular embodiments, the peptide analog of the invention has up to 30 amino acid residues.

The C—C chemokine receptor 3 protein (CCR3, also known as CD193) is a highly conserved protein that binds and responds to a variety of chemokines, including eotaxin (CCL11), eotaxin-2 (CCL24), eotaxin-3 (CCL26), MCP-3 (CCL7), MCP-4 (CCL13), MEC (CCL28) and RANTES (CCL5). The amino acid sequence of mammalian CCR3 proteins that are known and readily available from GEN-BANK include, but are not limited to, NP_847899.1 (*Homo sapiens*), XP_001149443.1 (*Pan troglodytes*), NP_001040605.1 (*Macaca mulatta*), NP_001005261.1 (*Canis lupus*), NP_001181889.1 (*Bos taurus*), NP_034044.3 (*Mus musculus*), NP_446410.1 (*Rattus norvegicus*), NP_001001620 (*Sus scrofa*) and NP_001128600 (*Oryctolagus cuniculus*). The CCR3 peptide analog of this invention is derived from mammalian CCR3 protein and includes all or a portion of the second transmembrane domain and a portion of the extracellular loop thereafter (Table 1).

TABLE 1

| Species | 2$^{nd}$ Transmembrane Domain/ Extracellular Loop Sequence | SEQ ID NO: |
|---|---|---|
| H. sapiens | LLNLAISDLLFLVTLPFWIHYVRGHNWVFGH | 5 |
| P. troglodytes | LLNLAISDLLFLFTLPFWIHYVRGHNWVFGH | 6 |
| M. mulatta | LLNLAISDLLFLFTLPFWIHYVRERNWVFSH | 7 |
| C. lupus | LLNLAISDLLFLFTLVFWIHYTGWNDWVFGR | 8 |
| B. taurus | LLNLAISDVLFLFTLPFWIHYVRWNEWVFGH | 9 |
| M. musculus | LFNLAISDLLFLFTVPFWIHYVLWNEWGFGH | 10 |
| R. norvegicus | LLNLAISDLLFLFTVPFWIHYVLWNEWGFGH | 11 |
| S. scrofa | LFNLAISDLLFLFTLPFWIHYILRKEWGFGH | 12 |
| O. cuniculus | LFNLAISDLLFLFTLPFWIHYVRWNEWVFDS | 13 |
| Consensus | LXNLAISDXLFLXTXXFWIHYXXXXXWXFXX | 14 |

A = Ala or alanine; R = Arg or arginine; N = Asn or asparagine; D = Asp or Aspartic acid; C = Cys or cysteine; E = Glu or glutamic acid; Q = Gln or glutamine; G = Gly or glycine; H = His or histidine; I = Ile or isoleucine; L = Leu or leucine; K = Lys or lysine; M = Met or methionine; F = Phe or phenylalanine; P = Pro or proline; S = Ser or serine; T = Thr or threonine; W = Trp or tryptophan; Y = Tyr or tyrosine; and V = Val or valine.

More specifically, the CCR3 peptide analog of this invention has a sequence including the transmembrane sequence Xaa$_1$-Leu-Phe-Leu-Xaa$_2$-Thr-Xaa$_3$-Xaa$_4$-Phe-Trp-Ile-His-Tyr (SEQ ID NO:15), wherein Xaa$_1$ denotes Val or Leu, Xaa$_2$ denotes Phe or Val, Xaa$_3$ denotes Leu or Val, and Xaa$_4$ denotes Pro or Val. In some embodiments, the CCR3 peptide analog of this invention is a 20 to 30 amino acid residue peptide including the transmembrane sequence of SEQ ID NO:15. In other embodiments, the CCR3 peptide analog includes the sequence LLFLVTLPFWIHY (SEQ ID NO:16). In further embodiments, the CCR3 peptide analog includes the sequence set forth in SEQ ID NO:15 or SEQ ID NO:16 and 1, 2, 3, 4, 5, 6, 7, 8, 9 or 10 additional consecutive amino acid residues as set forth in Table 1 on the N-terminus, C-terminus, or both. In certain embodiments, the CCR3 peptide analog includes the amino acid sequence LLNLAISDLLFLVTLPFWIHY (SEQ ID NO:17) or LLFLVTLPFWIHYVRGHNWVFGH (SEQ ID NO:18).

In certain embodiments, the CCR3 peptide analog of the invention further includes one or more deletions, additions, and/or substitutions of the native amino acid sequence yet retains at least one functional property of the native peptide.

For therapeutic use, the CCR3 peptide analog of this invention includes two or more modifications to the native CCR3 peptide sequence presented in Table 1, which increase resistance to proteolytic degradation, facilitate auto-assembly into nanoparticles, increase stability, increase solubility, increase shelf-life, increase bioavailability, reduce toxicity and/or facilitate insertion into a membrane. In particular, the CCR3 peptide analog includes two or more modifications selected from the group of lipidation, carboxylation, glycosylation, sulfonation, amidation, PEGylation, myristoylation, biotinylation, disulfide formation, and addition of charged amino acid residues. In some embodiments, the CCR3 peptide analog further includes an acetyl group at the N-terminus.

Lipidation of the CCR3 peptide analog refers to the covalent attachment of a lipophilic group to the CCR3 peptide. The lipophilic group can be a branched or straight chain saturated or unsaturated hydrocarbon including between about one to 90 carbons, for example between about 4 and 30 carbons, or alternatively between about 10 and 20 carbons, and is most preferably a $C_4$-$C_{30}$ straight chain hydrocarbon. Other lipophilic groups include steroids, terpenes, fat-soluble vitamins, phytosterols, terpenoids, phospholipids, glycerols, and natural or synthetic fats. The lipophilic group may be attached to the CCR3 peptide either directly or via a linking group. For example, 5-amino valeroic acid, 8-amino octanoic acid or 2-amino decanoic acid may be attached to the N- and/or C-terminus of the CCR3 peptide.

Carboxylation refers to the gamma-carboxylation of glutamic acid residues and glycosylation refers to the attachment of one or more sugars (e.g., N-acetylgalactosamine, galactose, mannose, GlcNAc, glucose, fucose or xylose) via N- or O-linkages to the CCR3 peptide. Sulfonation refers to the transfer of the sulfonate group ($SO_3^{-1}$) from 3'-phosphoadenosine-5'-phosphosulfate. Sulfonation can occur through several types of linkages, esters (O-sulfonation), amides (N-sulfonation) and thioesters (S-sulfonation).

Amidation refers to the addition of an amide group to the end of the polypeptide. Several methods for amidating a protein have been described including the use of an α-amidating enzyme (Beaudry, et al. (1990) *J. Biol. Chem.* 265 (29):17694-17699; U.S. Pat. No. 4,708,934); proteases (U.S. Pat. Nos. 4,709,014; 5,580,751); carbodiimide compounds, a trapping agent and an amine source (U.S. Pat. No. 5,503,989); and recombinant methods (WO 1998/050563). In particular embodiments, the CCR3 peptide analog of this invention includes C-terminal amidation.

The formation of a disulfide in a CCR3 peptide can include intramolecular or intermolecular disulfide bond formation between cysteine residues of one or two CCR3 peptides, respectively. In this respect, one or two cysteine residues can be introduced into a CCR3 peptide analog of this invention. Once the one or two cysteine residues are introduced into the peptide, the peptide may be subjected to an oxidative process using an oxidizing agent to form the disulfide bond between two cysteine residues. Oxidizing agents include, but are not limited to, air (du Vigneaud, et al. (1954) *J. Am. Chem. Soc.* 76:3115-21), potassium ferricyanide (Hope, et al. (1962) *J. Biol. Chem.* 237:1563-6), iodine (Flouret, et al. (1979) *Int. J. Pept. Prot. Res.* 13:137-41), thalium triflouroacetate (Fuji, et al. (1987) *J. Chem. Soc., Chem. Commun.* 21:1676-78) or dimethylsulfoxide (Tam, et al. (1991) *J. Am. Chem. Soc.* 113:6657-62). In particular embodiments, the CCR3 peptide analog of this invention includes a C-terminal cysteine residue for intermolecular disulfide formation.

"PEGylation" refers to the reaction in which at least one polyethylene glycol (PEG) moiety, regardless of size, is chemically attached to the CCR3 peptide to form a PEG-peptide conjugate. PEG, in its most common form, is a linear polymer having hydroxyl groups at each terminus: $HO-CH_2-CH_2O(CH_2CH_2O)_nCH_2CH_2-OH$, wherein $CH_2CH_2O$ represents the repeating monomer unit of PEG. In accordance with the present invention, a short linear PEG is attached to the C- and/or N-terminus of the CCR3 peptide.

In particular embodiments, the PEG component of the CCR3 peptide analog contains from 5 to 50 units of PEG monomers, i.e., $(-CH_2CH_2O-)_n$, wherein n is 5 to 50. In other embodiments, the CCR3 peptide analog includes up to 50, 45, 40, 35, 30, 25, 20, 15, 10 or 5 PEG units. In certain embodiments, the CCR3 peptide analog has between 20 and 30 PEG units. In a particular embodiment, the CCR3 peptide analog has up to 30 PEG units. PEG may be linked or attached to the C- and/or N-terminal amino acid residue of the CCR3 peptide via solid phase synthesis, e.g., by employing PEG building blocks such as O—(N-Fmoc-2-aminoethyl)-W-(2-carboxyethyl)-undecaethylene glycol available from commercial sources such as EMD Biosciences (La Jolla, Calif.).

Myristoylation refers to a lipidation modification where a myristoyl group, derived from myristic acid, is covalently attached by an amide bond to the N-terminus of the CCR3 peptide. This modification can be added either co-translationally or post-translationally with, e.g., N-myristoyltransferase (NMT) which catalyzes the myristic acid addition. In certain embodiments, the CCR3 peptide is myristoylated at the N-terminal amino acid residue in order to facilitate entry of the peptide into the cell.

In certain embodiments, the CCR3 peptide includes the addition of between 1 and 10 charged amino acid residues on the C-terminal end. A charged amino acid residue is intended to include aspartic acid (Asp or D) or glutamic acid (Glu or E), which contain an α-amino group that is in the protonated $-^+NH_3$ form under biological conditions. In particular embodiments, the CCR3 peptide includes between 1 and 7, 1 and 5, 1 and 4, or 1 and 3 charged amino acid residues on the C-terminal end. More particularly, the CCR3 peptide includes between 1 and 7, 1 and 5, 1 and 4, or 1 and 3 aspartic acid residues on the C-terminal end. Exemplary CCR3 peptide analogs including additional charged amino acid residues include LLNLAISDLLFLVTLPFWIHYDDDC (SEQ ID NO:19) and LLFLVTLPFWIHYVRGHNWVFGHDDD (SEQ ID NO:20)

Unless otherwise indicated, the above-referenced modifications of the CCR3 peptide analog can occur anywhere in the peptide sequence, including the peptide backbone, the amino acid side-chains, the N-terminus, C-terminus, or a combination thereof. In particular embodiments, modifications of the CCR3 peptide analog occur at the C-terminus of the CCR3 peptide.

In particular embodiments, the CCR3 peptide analog of the invention includes a combination of two or more of PEGylation, myristoylation, biotinylation, disulfide formation, and addition of charged amino acid residues. In a specific embodiment, the CCR3 peptide analog is amidated, PEGylated, and has additional charged amino acid residues. Exemplary CCR3 peptide analogs are provided in Table 2.

TABLE 2

| CCR3 peptide analog | SEQ ID NO: |
|---|---|
| LLFLVTLPFWIHYVRGHNWVFGHDDD-(CH$_2$CH$_2$O)$_{27}$—NH$_2$ | 21 |
| LLNLAISDLLFLVTLPFWIHYDDDC | 19 |
| LLFLVTLPFWIHYVRGHNWVFGHDDDC | 22 |
| LLNLAISDLLFLVTLPFWIHYDDD-(CH$_2$CH$_2$O)$_{27}$—NH$_2$ | 23 |

The CCR3 peptide of the invention can be synthesized recombinantly using recombinant DNA techniques. Thus, the invention also provides nucleic acids that encode the CCR3 peptide of the invention, as well as a vector, in particular an expression vector, that includes the nucleic acids encoding the CCR3 peptide of the invention. In certain embodiments, the vector provides replication, transcription and/or translation regulatory sequences that facilitate recombinant synthesis of the peptide in a eukaryotic cell (e.g., a yeast, insect or animal cell) or prokaryotic cell (e.g., *Escherichia coli, Bacillus subtilis*). Accordingly, the invention also provides host cells for recombinant expression of the peptide and methods of harvesting and purifying the CCR3 peptide produced by the host cells. Production and purification of recombinant peptides is routine practice to one of skilled in the art.

Alternatively, the CCR3 peptide of the invention can be chemically synthesized by any technique routinely used in the art, particularly solid-phase synthesis techniques, for example, using commercially-available automated peptide synthesizers. See, for example, Stewart & Young (1984) *Solid Phase Peptide Synthesis*, 2$^{nd}$ ed., Pierce Chemical Co.; Tam, et al. (1983) *J. Am. Chem. Soc.* 105:6442; Merrifield (1986) *Science* 232:341-347; Barany, et al. (1987) *Int. Peptide Protein Res.* 30:705-739; and U.S. Pat. No. 5,424,398, incorporated herein by reference.

In some embodiments, the peptide is fused to a protein or purification tag such as chitin binding protein, maltose binding protein, glutathione-S-transferase, 6His, FLAG, or HA, to facilitate detection and/or purification. By way of illustration, a Cys residue can be incorporated into the CCR3 peptide, wherein the N-terminal-side of the Cys residue is thioesterified and the tag is attached to the C-terminal-side. Upon purification, the tag is cut off and the peptide thioester is efficiently obtained.

The peptide can be purified by any suitable methods known in the art including, e.g., affinity chromatography, ion exchange chromatography, filter, ultrafiltration, gel filtration, electrophoresis, salting out, dialysis, and the like. In one embodiment, the CCR3 peptide is purified by reverse-phase chromatography. When the peptide of the invention is produced in the form of a fusion protein, the fusion moiety (or tag) can optionally be cleaved off using a protease before further analysis.

As indicated herein, the CCR3 peptide analog self-assembles in aqueous medium into highly homogenous nanoparticles. Dynamic light scattering analyses indicate that the radius of the instant nanoparticles is in the range of 1 to 100 nm, more specifically about 8 nm (FIG. 1). Based upon the size and composition, the nanoparticles facilitate translocation of the peptide through the plasma membrane and protect the peptide from degradation in the blood/serum or other body fluids. Accordingly, this invention also provides a nanoparticle composition containing the CC3 peptide analog as well as methods of using the nanoparticle composition to antagonize CCR3 and in the treatment of inflammatory diseases such as asthma, and eosinophilic esophagitis.

For therapeutic applications, the CCR3 peptide analog and nanoparticle thereof are preferably provided in pharmaceutical compositions containing an appropriate pharmaceutically acceptable carrier. Acceptable carrier materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS®, PEG, sorbitan esters, polysorbates such as POLYSORBATE 20 and POLYSORBATE 80, TRITON®, lecithin, or cholesterol); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, *Remington: The Science and Practice of Pharmacy*, Lippincott Williams & Wilkins, 21$^{st}$ edition (2005).

The primary vehicle or carrier in a pharmaceutical composition may be either aqueous or nonaqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can include Tris buffer of about pH 7.0-8.5 or acetate buffer of about pH 4.0-5.5, which may further include sorbitol or a suitable substitute thereof. Pharmaceutical compositions of the invention may be prepared for storage by mixing the selected composition having the desired degree of purity with optional formulation agents (*Remington: The Science and Practice of Pharmacy*, Id.) in the form of a lyophilized cake or an aqueous solution. Further, the CCR3 peptide analog and nanoparticle thereof may be formulated as a lyophilizate using appropriate excipients such as sucrose.

The pharmaceutical compositions provided herein can be specially formulated for oral administration in solid or liquid form or for intravenous injection. In this respect, the CCR3 peptide analog and nanoparticle thereof can be incorporated in a conventional systemic dosage form, such as a tablet, capsule, soft gelatin capsule, elixir or injectable formulation. The dosage forms may also include the necessary physiologically acceptable carrier material, excipient, lubricant, buffer, surfactant, antibacterial, bulking agent (such as mannitol), antioxidants (ascorbic acid or sodium bi sulfite) or the like.

Administration routes for the pharmaceutical compositions of the invention include orally; inhaled through nebulizers; topically applied by, e.g., eyedrops or nasal sprays; transdermally; through injection by intravenous, intraperitoneal, intracerebral (intraparenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The pharmaceutical compositions of the invention can be delivered parenterally. When parenteral administration is contemplated, the therapeutic compositions for use in this invention may be in the form of a pyrogen-free, parenterally acceptable aqueous solution containing the CCR3 peptide analog in a pharmaceutically acceptable vehicle. A particularly suitable vehicle for parenteral injection is sterile distilled water in which the CCR3 peptide analog is formulated as a sterile, isotonic solution, appropriately preserved. Preparation can involve the formulation of the CCR3 peptide analog with an agent, such as an injectable microsphere, a bio-erodible particle, a polymeric compound (such as polylactic acid or polyglycolic acid), a bead or liposome, that may provide controlled or sustained release of the product which may then be delivered via a depot injection. Formulation with hyaluronic acid has the effect of promoting sustained duration in the circulation. Implantable drug delivery devices may also be used to introduce the CCR3 peptide analog and nanoparticle thereof.

The pharmaceutical compositions of the invention can be delivered through the digestive tract, such as orally. In certain embodiments, the peptide is administered to the esophagus of the subject as an oral viscous preparation that is swallowed and coats the esophagus with said peptide. The CCR3 peptide analog and nanoparticle thereof may also be formulated with or without those carriers customarily used in the compounding of solid dosage forms such as tablets and capsules. A capsule may be designed to release the active portion of the formulation at the point in the gastrointestinal tract when bioavailability is maximized and presystemic degradation is minimized. Additional agents can be included to facilitate absorption of the CCR3 peptide analog disclosed herein. Diluents, flavorings, low melting point waxes, vegetable oils, lubricants, suspending agents, tablet disintegrating agents, and binders may also be employed. These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like.

In particular embodiments, the CCR3 peptide analog and nanoparticle thereof are optimized for aerosol delivery, particularly to the respiratory tract, as an inhaled medication, the advantages being local delivery and better tissue penetration. In this respect, a solution of the CCR3 peptide analog and nanoparticle thereof is administered to the lungs of the subject via nebulization, using a drug delivery device (nebulizer) to administer medication in the form of a mist inhaled into the lungs using a mouthpiece or mask. In order to assure proper particle size in a liquid aerosol, particles can be prepared in respirable size and then incorporated into a colloidial dispersion either containing a propellant as a metered dose inhaler (MDI) or air, such as in the case of a dry powder inhaler (DPI). The active ingredient is provided in a pressurized pack with a suitable propellant such as a chlorofluorocarbon (CFC) (e.g., dichlorodifluoromethane, trichlorofluoromethane, or dichlorotetrafluoroethane), carbon dioxide or other suitable gas. The dose of drug can be controlled by a metered valve.

Alternatively, the active ingredients can be provided in a form of a dry powder, for example a powder mix of the peptide in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges, of e.g., gelatin or blister packs from which the powder can be administered by means of an inhaler.

Alternatively, formulations can be prepared in solution form in order to avoid the concern for proper particle size in the formulation. Solution formulations must nevertheless be dispensed in a manner that produces particles or droplets of respirable size. For MDI application, once prepared an aerosol formulation is filled into an aerosol canister equipped with a metered dose valve. In the hands of the patient the formulation is dispensed via an actuator adapted to direct the dose from the valve to the patient.

Generally, the formulations of the invention can be prepared by combining (i) the CCR3 peptide analog and nanoparticle thereof in an amount sufficient to provide a plurality of therapeutically effective doses; (ii) the fluid, e.g., propellant, in an amount sufficient to propel a plurality of doses, e.g., from an aerosol canister; (iii) optionally, the water addition in an amount effective to further stabilize each of the formulations; and (iv) any further optional components, e.g., ethanol as a cosolvent; and dispersing the components. The components can be dispersed using a conventional mixer or homogenizer, by shaking, or by ultrasonic energy as well as by the use of a bead mill or a microfluidizer. Bulk formulations can be transferred to smaller individual aerosol vials by using valve to valve transfer methods, pressure filling or by using conventional cold-fill methods. It is not required that a component used in a suspension aerosol formulation be soluble in the fluid carrier, e.g., propellant. Components that are not sufficiently soluble can be coated or congealed with polymeric, dissolution controlling agents in an appropriate amount and the coated particles can then be incorporated in a formulation as described above. Polymeric dissolution controlling agents suitable for use in this invention include, but not limited to polylactide glycolide co-polymer, acrylic esters, polyamidoamines, substituted or unsubstituted cellulose derivatives, and other naturally derived carbohydrate and polysaccharide products such as zein and chitosan.

Aerosol canisters equipped with conventional valves, preferably metered dose valves, can be used to deliver the formulations of the invention. It has been found, however, that selection of appropriate valve assemblies for use with aerosol formulations is dependent upon the particular component and other adjuvants used (if any), on the fluid, e.g., propellant, and on the particular drug being used. Conventional neoprene and buna valve rubbers used in metered dose valves for delivering conventional CFC formulations often have less than optimal valve delivery characteristics and ease of operation when used with formulations containing HFC-134a (1,1,1,2-tetrafluoroethane) or HFC-227 (1,1,1,2,3,3,3-heptafluoropropane). Therefore, certain formulations of the invention are preferably dispensed via a valve assembly wherein the diaphragm is made of a nitrile rubber such as DB-218 (American Gasket and Rubber, Schiller Park, Ill.) or an EPDM rubber such as VISTALON® (Exxon), ROYALENE® (UniRoyal), bunaEP (Bayer). Also suitable are diaphragms fashioned by extrusion, injection, molding or compression molding from a thermoplastic elastomeric material, such as FLEXOMER® GERS 1085 NT polyolefin (Union Carbide).

Conventional aerosol canisters, coated or uncoated, anodized or unanodized, e.g., those of aluminum, glass, stainless steel, polybutyl or polyethylene terephthalate, and coated canisters or cans with epon, epoxy, etc., can be used to contain a formulation of the invention.

Given that the CCR3 peptide analog of this invention assembles into a nanoparticle, the nanoparticle can advantageously be used to deliver one or more additional therapeutic agents. Accordingly, in certain embodiments, the nanoparticle composition further includes at least one second therapeutic agent. Second therapeutic agents include, but are not limited to, steroidal drugs (e.g., aldosterone, beclometasone, betamethasone, deoxycorticosterone acetate, fludrocortisone, hydrocortisone (cortisol), prednisolone, prednisone, methylprednisolone, dexamethasone, and triamcinolone); antibacterial agents (e.g., amoxicillin, carbenicillin, cefaclor, ciprofloxacin, clarithromycin, clindamycin, doxycycline, erythromycin, gentamicin, kanamycin, minocycline, neomycin, penicillin, polymyxin B, rifampin, streptomycin, sulfacetamide, tetracycline, ticarcillin and tobramycin); antifungal agents (e.g., amphotericin B, ciclopirox, clotrimazole, econazole, fluconazole, nystatin and oxyconazole); anticoagulants (e.g., acenocoumarol, argatroban, bivalirudin, lepirudin, fondaparinux, heparin, phenindione, warfarin and ximelagatran); thrombolytics (e.g., anistreplase, reteplase, t-PA (alteplase activase), streptokinase, tenecteplase and urokinase), non-steroidal anti-inflammatory agents (e.g., aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid and tolmetin), and antiplatelet agents (e.g., abciximab, cilostazol, clopidogrel, dipyridamole, ticlopidine and tirofibin.

The CCR3 peptide analog and nanoparticle thereof can also be administered in combination with other classes of compounds, including, but not limited to, (1) alpha-adrenergic agents; (2) antiarrhythmic agents; (3) anti-atherosclerotic agents, such as ACAT inhibitors; (4) anticancer agents and cytotoxic agents, e.g., alkylating agents, such as nitrogen mustards, alkyl sulfonates, nitrosoureas, ethylenimines, and triazenes; (5) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (6) antimetabolites, such as folate antagonists, purine analogues, and pyrimidine analogues; (7) antiproliferatives, such as methotrexate, FK506 (tacrolimus), and mycophenolate mofetil; (8) anti-TNF antibodies or soluble TNF receptor, such as etanercept, rapamycin, and leflunimide; (9) aP2 inhibitors; (10) bile acid sequestrants, such as questran; (11) calcium channel blockers, such as amlodipine besylate; (12) chemotherapeutic agents; (13) cyclooxygenase-2 (COX-2) inhibitors, such as celecoxib and rofecoxib; (14) cyclosporins; (15) cytotoxic drugs, such as azathioprine and cyclophosphamide; (16) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (17) endothelin converting enzyme (ECE) inhibitors, such as phosphoramidon; (18) enzymes, such as L-asparaginase; (19) Factor VIIa Inhibitors and Factor Xa Inhibitors; (20) farnesyl-protein transferase inhibitors; (21) fibrates; (22) growth factor inhibitors, such as modulators of PDGF activity; (23) growth hormone secretagogues; (24) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (25) hormonal agents, such as glucocorticoids (e.g., cortisone), estrogens/antiestrogens, androgens/antiandrogens, progestins, and luteinizing hormone-releasing hormone antagonists, and octreotide acetate; (26) immunosuppressants; (27) mineralocorticoid receptor antagonists, such as spironolactone and eplerenone; (28) microtubule-disruptor agents, such as ecteinascidins; (29) microtubule-stabilizing agents, such as pacitaxel, docetaxel, and epothilones A-F; (30) MTP Inhibitors; (31) niacin; (32) phosphodiesterase inhibitors, such as PDE III inhibitors (e.g., cilostazol) and PDE V inhibitors (e.g., sildenafil, tadalafil, and vardenafil); (33) plant-derived products, such as vinca alkaloids, epipodophyllotoxins, and taxanes; (34) platelet activating factor (PAF) antagonists; (35) platinum coordination complexes, such as cisplatin, satraplatin, and carboplatin; (36) potassium channel openers; (37) prenyl-protein transferase inhibitors; (38) protein tyrosine kinase inhibitors; (39) renin inhibitors; (40) squalene synthetase inhibitors; (41) TNF-alpha inhibitors, such as tenidap; (42) thrombin inhibitors, such as hirudin; (43) thromboxane receptor antagonists, such as ifetroban; (44) topoisomerase inhibitors; (45) vasopeptidase inhibitors (dual NEP-ACE inhibitors), such as omapatrilat and gemopatrilat; (46) beta-adrenergic agents, such as carvedilol and metoprolol; and (47) other miscellaneous agents, such as, hydroxyurea, procarbazine, mitotane, hexamethylmelamine, and gold compounds.

Chemokine receptors have been implicated as being important mediators of inflammatory, infectious, and immunoregulatory disorders and diseases, including asthma and allergic diseases, as well as autoimmune pathologies such as rheumatoid arthritis, Grave's disease, chronic obstructive pulmonary disease, age-related macular degeneration, and atherosclerosis. In particular, CCR3 is expressed on eosinophils, basophils, TH2 cells, alveolar macrophages, mast cells, epithelial cells, microglia cells, astrocytes and fibroblasts and plays a pivotal role in attracting eosinophils to sites of allergic inflammation and subsequently activating the same. Eosinophils have been implicated in the pathogenesis of a number of allergic diseases, such as bronchial asthma (Durham & Kay (1985) Clin. Allergy 15:411-418; Kroegel, et al. (1994) J. Allergy Clin. Immunol. 93:725-734), allergic rhinitis (Durham (1998) Clin. Exp. Allergy 28 (Suppl. 2):11-16), atopic dermatitis (Leung (1999) J. Allergy Clin. Immunol. 104:S99-108), eosinophilic esophagitis, and eosinophilic gastroenteritis (Bischoff, et al. (1999) Am. J. Gastro. 94:3521-3529). Therefore, CCR3 antagonists are of use in the treatment of inflammatory diseases, such as allergic asthma and allergic rhinitis mediated by eosinophils. In addition, CCR3 antagonists are also of use in blocking infection of CCR3 expressing cells by infectious agents, such as HIV, as CCR3 is known to be an entry co-receptor for such infectious agents.

Accordingly, the present invention is also a method of treating, preventing, or ameliorating one or more symptoms of an eosinophil- or CCR3-mediated disease or condition in a subject by administering to the subject an effective amount of the CCR3 peptide analog or nanoparticle thereof described herein. In one embodiment, the subject is a mammal. In another embodiment, the subject is a human. In contrast to small molecule antagonists, the CCR3 peptide analog of this invention does not inhibit ligand-induced CCR3 internalization and degradation. Therefore, the CCR3 peptide analog is a biased antagonist that can be used without the development of resistance.

"Treating" a mammal having a disease or condition means accomplishing one or more of the following: (a) reducing the severity of the disease or condition; (b) arresting the development of the disease or condition; (c) inhibiting worsening of the disease or condition; (d) limiting or preventing recurrence of the disease or condition in patients that have previously had the disease or condition; (e) causing regression of the disease or condition; (f) improving or eliminating the symptoms of the disease or condition; and (g) improving survival.

As used herein, the term "amount effective," "effective amount" or a "therapeutically effective amount" refers to an amount of the CCR3 peptide analog or nanoparticle of the invention or a pharmaceutical composition comprising the same that is sufficient to achieve the stated desired result. In certain embodiments, an effective amount is an amount that inhibits CCR3 signal transduction including activation of Gαd and phosphorylation of ERK1/2 in response to eotaxin or RANTES stimulation. Further, an effective amount is an amount that attenuates CCR3-mediated chemotaxis and degranulation in vitro and in vivo.

The amount of the CCR3 peptide analog or nanoparticle which constitutes an "effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 100 mg/kg, or 1 µg/kg up to about 100 mg/kg, or 5 µg/kg up to about 100 mg/kg.

Eosinophil- or CCR3-mediated diseases or conditions that can be treated in accordance with this method include, but are not limited to asthma, atopic dermatitis, allergic rhinitis, psoriasis, eosinophilic esophagitis (EoE), eosinophilic gastrointestinal diseases (EGIDs) including eosinophilic gastritis (EG), eosinophilic gastroenteritis (EGE) and eosinophilic colitis (EC), and other diseases including eosinophilic fasciitis (EF), eosinophilic bronchitis, eosinophilic cystitis, eosinophilic pneumonia, the hypereosinophilic syndrome (HES) and variants thereof, Eosinophilic Granulomatosis with Polyangiitis (aka Churg-Strauss Syndrome), eosinophilic cellulitis (Wells Sydrome), eosinophil myalgia syndrome, chronic rhinosinusitis (CRS) and eosinophil-associated parasite and fungal diseases, e.g., allergic bronchopulmonary aspergillosis (ABPA), and the like, as well as multiple sclerosis, human immunodeficiency virus (HIV), age-related macular degeneration (AMD) and cancer including, but not limited to prostate cancer, liver cancer skin cancer, ovarian cancer, uterine cancer, kidney cancer (RCC) and Hodkin's lymphoma. The disease or condition may also include food allergies, inflammatory bowel disease, ulcerative colitis, Crohn's disease, mastocytosis, hyper IgE syndrome, systemic lupus erythematous, acne, allograft rejection, reperfusion injury, chronic obstructive pulmonary disease, sinusitis, basophilic leukemia, chronic urticaria, basophilic leukocytosis, eczema, COPD (chronic obstructive pulmonary disorder), arthritis, rheumatoid arthritis, psoriatic arthritis, and osteoarthritis. In certain embodiments, the disorder or condition is asthma, exercise induced asthma or EoE.

The invention is described in greater detail by the following non-limiting examples.

Example 1: Materials and Methods

Reagents.

Recombinant human CCL5, CCL11, CCL13, CCL24, CCL26 and CCL28 were purchased from BioLegend (San Diego, Calif.). Small molecule CCR3 antagonists, SB238437 and UCB35625, were purchased from Tocris Bioscience (Bristol, UK). PD184161, chloroquine, MG132, and forskolin were purchased from Cayman Chemical (Ann Arbor, Mich.).

Cell Culture.

AML14.3D10-CCR3 (ATCC, Manassas, Va.; Daugherty, et al. (1996) *J. Exp. Med.* 183:2349-2354) were maintained in RPMI-1640 supplemented with 10% FBS, 1.5 g/L sodium bicarbonate, 4.5 g/L glucose, 2 mM L-glutamine, 10 mM HEPES, 1 mM sodium pyruvate, 50 µM β-mercaptoethanol, and 2 mg/ml G418 in a humidified incubator with 5% $CO_2$ at 37° C.

Eosinophil Purification.

Blood eosinophils were purified from anti-coagulated blood drawn from mild allergic asthmatic subjects. Peripheral blood was subjected to density gradient centrifugation over FICOLL-PAQUE® Plus (GE Healthcare, Pittsburgh, Pa.) media to obtain a pellet containing erythrocytes and granulocytes. After erythrocyte lysis via hypotonic shock, eosinophils were purified by negative selection using a cocktail of antibody-conjugated magnetic beads against non-eosinophils (Miltenyi Biotec, Auburn, Calif.). The eosinophils were resuspended in X-VIVO 10 without phenol red. The purity and viability of the eosinophils obtained was routinely >97% as assessed by Hema III and trypan blue staining, respectively.

Signal Transduction Assay—Western Blotting.

AML14.3D10-CCR3 cells were serum starved for 16 hours. Cells were pretreated with vehicle control, R3-2-1 or PD184161 for 30 minutes at 37° C., and subsequently stimulated with 8 nM CCL5 or CCL11 for 2 minutes. Stimulation was stopped by adding ice cold PBS. Cells were centrifuged and lysed in RIPA buffer containing protease and phosphatase inhibitors. Cell lysates were resolved on a 12% SDS-PAGE gel (10 µg/lane), transferred to PVDF membrane and blocked in 5% milk. Phospho-ERK1/2 was detected using rabbit monoclonal antibody (clone D13.14.4E, Cell Signaling Technology, Danvers, Mass.) and secondary goat anti-rabbit IgG-HRP (Santa Cruz Biotechnology, Dallas, Tex.). As a loading control, the membrane was subsequently stripped and re-probed with an antibody against total ERK1/2 (clone 127F5, Cell Signaling Technology).

Chemotaxis Assay.

Cell migration was determined using a 96-well TRANSWELL® system (Corning, Tewksbury, Mass.). Briefly, 200 µl chemoattractant or control medium was added to the lower chamber while 100 µl cells were added to the upper chamber. The two chambers were separated by a polycarbonate filter with 5 µm pores. For AML14.3D10-CCR3 cells, $2 \times 10^5$ cells/well were resuspended in RPMI-1640+ 0.1% BSA and allowed to migrate for 4 hours at 37° C. For blood eosinophils, $1 \times 10^5$ cells/well were resuspended in X-VIVO 10+0.5% BSA and allowed to migrate for 3 hours at 37° C. Migrated cells were counted using a Beckman QUANTA SC flow cytometer. All experiments were performed in duplicate. Checkerboard analysis was done to distinguish chemotaxis from chemokinesis.

Receptor Expression and Internalization.

To assess surface expression of CCR3, cells were stained using PE-conjugated anti-human CCR3 antibody (clone 5E8, BioLegend) or PE-conjugated isotype-matched control after blocking with 10% human AB serum. To determine ligand-induced CCR3 internalization, cells were incubated with various chemokines for 1 hour at 37° C., washed once in staining buffer (PBS+0.5% BSA+0.1% $NaN_3$) before being stained as above. After antibody staining, cells were fixed in 2% paraformaldehyde and analyzed on a QUANTA SC flow cytometer (Beckman Coulter, Indianapolis, Ind.).

Gαi Activation.

GTP-bound Gαi was detected using a commercial Gαi assay kit (Abcam, Cambridge, Mass.) with modifications. Briefly, AML14.3D10-CCR3 cells were serum-starved for 16 hours before being pretreated with 2 mg/ml pertussis toxin for 2 hours, 10 µM R3-2-1 for 30 minutes, or with vehicle control. Pretreated cells were then stimulated with 8 nM CCL11 or medium for 1 minute. The reaction was stopped by adding ice cold PBS. Ten (10) million cells were used for each condition. Washed cells were lysed with 1× lysis buffer following manufacturer instructions. For pull-down of active Gαi, mouse anti-GTP bound Gαi antibody was conjugated to DYNABEADS Protein G (Life Technologies, Carlsbad, Calif.) for 15 minutes at room temperature. Conjugated beads were washed 3 times with Tris-buffered saline+TWEEN® polysorbate (TBST) and incubated with cell lysates for 20 minutes at room temperature. After washing with TBST, bound proteins were eluted by boiling the beads in 2×SDS buffer for 5 minutes. Eluates were resolved by SDS-PAGE and immunoblotted using a polyclonal rabbit anti-total Gαi antibody (Cell Signaling Technology).

CCR3 Degradation.

AML14.3D10-CCR3 cells were resuspended in RPMI-1640+0.1% BSA. Aliquots of $1 \times 10^6$ cells were pretreated with 10 µM cycloheximide for 1 hour at 37° C. Some cells were concurrently pretreated with 10 µM R3-2-1, 10 µM MG132, or both for 30 minutes. Pretreated cells were stimulated with 8 nM eotaxin or RANTES for 3 hours to induce receptor degradation. An aliquot of untreated cells were reserved at the start of the experiment to establish baseline CCR3 expression. All cells were then lysed in RIPA buffer and immunoblotted for CCR3 with a polyclonal rabbit anti-CCR3 antibody (Abcam) followed by goat anti-rabbit IgG-HRP secondary antibody (Santa Cruz).

Example 2: Design of R3-2-1

The monomeric R3-2-1 peptide was derived from the primary sequence of the second transmembrane domain and first intracellular loop regions of CCR3 with two chemical modifications. First, three aspartate residues were added to the carboxyl terminus. Second, the last aspartate residue was covalently linked to 27 units of polyethylene glycol (PEG). R3-2-1 monomers self-assembled in aqueous environment into nanospheres with a hydrodynamic radius of approximately 8 nm (FIG. 1). This nanospherical structure was maintained over a wide range of monomeric concentrations.

Example 3: R3-2-1 Inhibits Chemotaxis Induced by Multiple CCR3 Ligands

Figure 3:
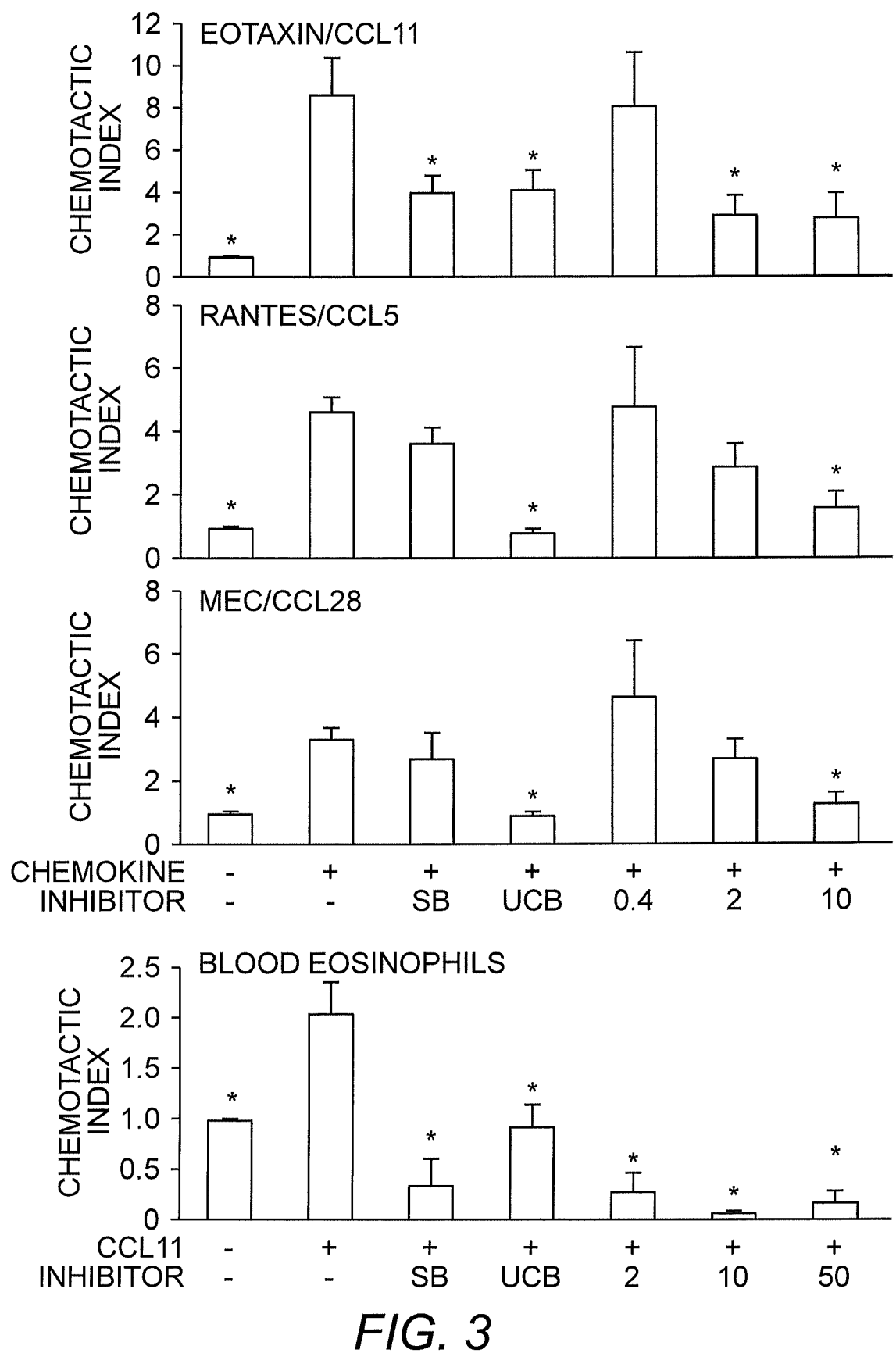
FIG. 3 shows that R3-2-1 inhibits CCR3-mediated chemotaxis induced by multiple ligands. In AML14.3D10-CCR3 cells, R3-2-1 (0.4, 2 or 10 µM) inhibits chemotaxis induced by Eotaxin/CCL11, RANTES/CCL5 and MEC/CCL28 in a dose-dependent fashion. R3-2-1 (2, 10 or 50 µM) is similarly able to inhibit chemotaxis of blood eosinophils. SB: SB328437, competitive CCR3 inhibitor. UCB.

Primary eosinophils and the stable CCR3+eosinophilic myelocytic cell line, AML14.3D10-CCR3 (Daugherty, et al. (1996) *J. Exp. Med.* 183:2349-2354) undergo CCR3-mediated chemotaxis induced by multiple chemokines including eotaxin/CCL11, RANTES/CCL5, MCP-4/CCL13, and MEC/CCL28 (Daugherty, et al. (1996) *J. Exp. Med.* 183: 2349-2354; Pan, et al. (2000) *J. Immunol.* 165:2943-2949). R3-2-1 functionally inhibits CCR3-mediated chemotaxis of both AML14.3D10-CCR3 and blood eosinophils in a dose-dependent fashion at concentrations comparable to UCB35625, a small molecule non-selective CCR3 inhibitor (FIG. 3). The competitive CCR3 inhibitor SB328437 only inhibits CCL11-induced but not CCL5- or CCL28-induced chemotaxis (FIG. 2). In addition, R3-2-1 inhibits chemotaxis of both AML14.3D10-CCR3 and blood eosinophils induced by CCL11/Eotaxin-1, CCL24/Eotaxin-2, and CCL26/Eotaxin-3 in a dose-dependent fashion (Table 3). By comparison, the R-3-2-3 scramble peptide control did not inhibit CCL11-, CCL24-, or CCL26-induced chemotaxis of blood eosinophils. Most notably, this analysis shows that the $IC_{50}$ for R3-2-1 is in the low nanomolar range.

TABLE 3

| | Blood eosinophils | | AML14.3D10-CCR3 cells | |
|---|---|---|---|---|
| | $IC_{50}$ (µM) | $IC_{90}$ (µM) | $IC_{50}$ (µM) | $IC_{90}$ (µM) |
| CCL11 | 0.11 ± 0.01 | 0.76 ± 0.10 | 0.21 ± 0.04 | 1.75 ± 0.20 |
| CCL24 | 0.08 ± 0.01 | 0.73 ± 0.10 | 0.14 ± 0.02 | 0.89 ± 0.12 |
| CCL26 | 0.16 ± 0.02 | 1.10 ± 0.15 | 0.10 ± 0.01 | 0.78 ± 0.10 |

*R3-2-1 (0.001-10 µM), CCL11/Eotaxin-1 (12 nM), CCL24/Eotaxin-2 (20 nM), and CCL26/Eotaxin-3 (100 nM) for 4 hours.

Example 4: Effects of R3-2-1 on CCR3 Signal Transduction Pathways

CCR3 is coupled to the pertussis toxin-sensitive G protein Gαi (Elsner, et al. (1996) *Eur. J. Immunol.* 26:1919-1925). Upon ligand binding and activation, the now active GTP-bound Gαi and the Gβγ dimer dissociate from CCR3 to trigger downstream signaling cascades including the MAPK (ERK1/2, p38) pathways and the PI3K/AKT pathway. R3-2-1 was found to inhibit the activation of Gαi using an immunoprecipitation assay that specifically detects the GTP-bound form of Gαi (FIG. 2A). The subsequent phosphorylation of ERK1/2 was also attenuated by R3-2-1 (FIG. 2B).

Example 5: Biased Antagonism of CCR3 by R3-2-1

Concurrent to ligand binding and activation, CCR3 undergoes ligand-induced desensitization and internalization (Zimmermann, et al. (1999) *J. Biol. Chem.* 274:12611-12618). As part of the desensitization process, CCR3 is degraded. This is thought to occur via β-arrestin recruitment to phosphorylated CCR3 and subsequent sequestration of the receptor into endosomal compartments, eventually leading to degradation. β-arrestin signaling is central in this process and is characterized by a late activation of signaling pathways such as MAPK/ERK1/2, in contrast to acute activation by G proteins. Analysis of acute (2-5 minutes) and late (30 minutes) phase phosphorylation of ERK1/2 indicates that the R3-2-1 (10 µM) inhibits only acute phosphorylation of ERK1/2. By comparison, the R3-2-3 scrambled peptide control (10 µM), does not inhibit either acute or late phase phosphorylation, SB328437 (10 µM) inhibits both acute and late phase phosphorylation, and UCB35625 (10 µM) inhibits the late phase to a higher degree than the early phase phosphorylation. Therefore, the R3-2-1 peptide is a biased antagonist in that it inhibits the early phase but not late-phase of CCL11 ligand-induced β-arrestin signaling, whereas the small molecule inhibitors are unbiased antagonists.

Inhibition of β-arrestin signaling may interfere with effective degradation and therefore hasten re-sensitization of cells with the receptor. Indeed, small molecule CCR3 antagonists partially or completely block ligand-induced CCR3 internalization (Sabroe, et al. (2005) *Eur. J. Immunol.* 35:1301-1310), while R3-2-1 does not (FIG. 4A). Interestingly, R3-2-1 seems to induce CCR3 internalization on its own in AML14.3D10-CCR3 cells (FIG. 4B) without itself being an agonist for chemotaxis (FIG. 4C). Indeed, R3-2-1 alone decreases CCR3 surface expression in AML14.3D10-CCR3 cells, reaching significant internalization levels at a 1 µM concentration. Further, when added concurrently with 12 nM CCL11, neither R3-2-1 (1 µM) nor R3-2-3 (1 µM) interfere with CCL11-induced receptor internalization, whereas both SB328437 (1 µM) and UCB35625 (1 µM) significantly inhibit chemokine-induced CCR3 internalization.

To elucidate the fate of CCR3 following ligand-induced internalization and R3-2-1 treatment, CCR3 protein levels of cycloheximide-treated eosinophilic cells were analyzed. CCR3 was found to be degraded following ligand exposure, in keeping with previous reports (Zimmermann, et al. (1999) *J. Biol. Chem.* 274:12611-12618; Wise, et al. (2010) *J. Allergy Clin. Immunol.* 126:150-7.e2). R3-2-1 enhanced CCR3 degradation induced by eotaxin and RANTES. To further analyze this aspect, AML14.3D10-CCR3 cells were treated for 24, 48 or 72 hour with R3-2-1 or unbiased antagonists SB328437 and UCB35625 (all at 1 µM), with or without CCL11 (12 nM). This analysis confirmed that R3-2-1 peptide promotes CCR3 internalization, rather than surface accumulation as occurs with the small molecule inhibitors SB328437 and UCB35625, and does not induce "tolerance" to inhibition of CCL11-induced chemotaxis over a period of 72 hours. That is, the small molecule unbiased antagonists SB328437 and UCB35625 slowly lose their ability to antagonize CCL11-induced chemotaxis, compared to R3-2-1, which retains it full inhibitory activity over the same time period.

Example 6: R3-2-1 Inhibits Eosinophil Recruitment in a Mouse Model of EoE

To demonstrate in vivo efficacy of R3-2-1 for blocking eosinophil recruitment into sites of allergic inflammation, L2-IL5 transgenic mice (Masterson, et al. (2014) *Gut* 63:43-53) were sensitized and challenged with oxazalone (OXA) according to an established protocol (FIG. 5A). Mice were treated i.v. with R3-2-1 peptide, scrambled R3-2-3 control peptide (YLFLLVTVFHIWLPHNRGHVWGFDDD-$PEG_{27}$-$NH_2$; SEQ ID NO:24), or the allosteric non-selective CCR3 inhibitor, UCB35625. Eosinophil recruitment into the esophageal epithelium was assessed 24 hours after the last OXA challenge by counting eosinophils in 9 high power fields (hpf) covering the total esophagus or 3 hpf covering the distal esophagus. R3-2-1 significantly reduced eosinophil recruitment relative to the control scrambled peptide into both the distal and total esophageal epithelium (FIGS. 5B and 5C, respectively), where the highest density of eosinophils occur in this EoE model. In contrast, the CCR3 antagonist UCB35625 was ineffective in reducing eosinophil recruitment in this EoE model, even though it was a potent inhibitor of chemotaxis induced by multiple CCR3 agonists in vitro, similar to R3-2-1.

Example 7: R3-2-1 Physically Interacts with Human CCR3

Ligand binding to GPCR induces conformational transitions in the receptor that activate G-proteins and β-arrestin recruitment. NMR evaluation of the binding of R3-2-1 and CCL11/eotaxin-1 to CCR3 membrane preparations show chemical shift changes indicative of binding of R3-2-1 to CCR3 in the presence of CCL11 (FIGS. 6A-6E). Because R3-2-1 is an analog of the second transmembrane helix of CCR3, it is expected that R3-2-1 competes with the native helix 2 for binding to helices 1 and 3. Binding to helix 3 may disrupt the structure and orientation of the DRY motif in intracellular loop 2, inhibiting G-proteins.

Example 8: Pre-Clinical Testing of R3-2-1 in a Triple Antigen Asthma Model

In the triple antigen driven allergic mouse model, mice are sensitized and airway-challenged with a combination of aeroallergens including Dust mite, Ragweed and *Aspergillus* sp. (DRA; Goplen, et al. (2009) *J. Allergy Clin. Immunol.* 123:925-932). This model recapitulates many of the pathologic features of human asthma, including eosinophil recruitment into the lung and airspaces, eosinophil degranulation, increased expression of Th2 cytokines, airway hyperreactivity (AHR), and airway remodeling (goblet cell metaplasia and mucus overproduction), and airway smooth muscle hyperplasia and subepithelial fibrosis. Using this model, the effectiveness of R3-2-1 in blocking allergen-induced eosinophil recruitment into the airways and development of airway pathologies in mice was evaluated. It was determined whether systemic (i.v.) administration of R3-2-1 nanoparticles has the capacity to inhibit eotaxin-mediated eosinophil recruitment into the airways. Mice subjected to the triple antigen (DRA) protocol were treated with R3-2-1, scrambled peptide (R3-2-3) and vehicle controls via i.v. administration following antigen sensitization, 24 hours prior to the first allergen challenge on Day 11 of the protocol (FIG. 7), and for i.v. routes, repeated before each subsequent allergen challenge.

The results of this analysis indicated that the CCR3 R3-2-1 peptide significantly reduced eosinophil recruitment into the airspaces in the triple allergen mouse asthma model of allergic airway inflammation. In particular, the inhibitory effect of R3-2-1 was dose-dependent with a maximum 69.3% reduction in mice treated with 12 mg/kg R3-2-1 compared to vehicle and R3-2-3 scrambled peptide controls (FIG. 8). Further, R3-2-1 significantly inhibited the total number of eosinophils recruited into the lung airspaces in a dose-dependent manner (FIG. 9) with an $IC_{50}$ of 8.16 mg/kg (Table 4).

TABLE 4

| Dose (mg/kg) | % Inhibition |
|---|---|
| 3 | 19.54 ± 14.81 |
| 6 | 44.24 ± 9.33 |
| 9 | 53.03 ± 10.82 |
| 12 | 69.33 ± 4.20 |

These results demonstrate in vivo efficacy of the CCR3 R3-2-1 peptide in the mouse eosinophilic asthma model of allergic airway inflammation.

Example 9: Pre-Clinical Testing of R3-2-1 in an IL-5/CCL24 Transgenic Severe Asthma Mouse The possibility that co-expression of both IL-5 and CCR3 ligands is required for airway eosinophilia and asthma pathologies led to the development of the IL-5/CCL24 double transgenic asthma model using mice with systemic expression of IL-5 (Lee, et al. (1997) *J. Exp. Med.* 185: 2143-2156) crossed with mice in which lung-specific expression of CCL24 used the Clara cell CC10 promoter (Ochkur, et al. (2007) *J. Immunol.* 178:7879-7889). The asthma pathologies that occur in all IL-5/CCL24 transgenic mice are more substantial than those induced in any of the sensitization/challenge models, and are completely eliminated by crosses with eosinophil-deficient PHIL mice (Lee, et al. (2004) *Science* 305:1773-1776). These "asthmatic" mice are ideal to test the efficacy of R3-2-1 instilled directly into the airways or systemically to antagonize CCL24 from the airways/lungs to inhibit eosinophil recruitment and its consequent pathologies. IL-5/CCL24 mice are treated with R3-2-1 (or peptide and vehicle controls) i.n. and/or i.v. (or i.p.) daily for 1-2 weeks, followed by quantitative assessments of airway eosinophils and eosinophil peroxidase (EPX) activity in BALF (=eosinophil degranulation), mucus production, and CCL24 levels as described (Ochkur, et al. (2007) *J. Immunol.* 178:7879-7889; Lee, et al. (2004) *Science* 305:1773-1776; Justice, et al. (2003) *Am. J. Physiol. Lung Cell. Mol. Physiol.* 284:L169-178). EPX activity and CCL24 levels are determined using ELISA kits (R&D Systems, Cell Technologies, Inc.). Mucus over-production is measured in BALF, as discussed above and the scrambled R3-2-1 peptide is the control. Lungs are inflation fixed, sectioned and stained for mMBP-1 to quantitate tissue and airway eosinophils, and extracellular MBP-1 (=degranulation), and for goblet cells/mucus production by PAS staining. Results are evaluated as means±SEM, and analyzed using ANOVA followed by analyses of the differences between means for 10 mice/experimental group using the appropriate parametric or non-parametric tests, considered significant at $p<0.05$. The results of this analysis will demonstrate that mice administered that R3-2-1 peptide can be rescued from some or all of their asthma phenotypes.

Example 10: Analysis of Other CCR3 Transmembrane Peptides

Linear peptides derived from the amino acid sequence of each transmembrane domain of human CCR3 were designed (Table 5). Minor chemical modifications such as acetylation were made to enhance solubility in aqueous buffers.

TABLE 5

| Peptide | Sequence (N->C) | SEQ ID NO: |
|---|---|---|
| TM1 | Ac-KDDDQFVPPLYSLVFTVGLLGNVVVVMILI | 25 |
| TM2 | LLNLAISDLLFLVTLPFWIHYDDDC | 19 |
| TM3 | Ac-KDDDLLSGFYHTGLYSEIFFIILLTI | 26 |
| TM4 | Ac-VTFGVITSIVTWGLAVLAALPEFIFDDDK | 27 |
| TM5 | CDDDTIFCLVLPLLVMAICYTGII | 28 |
| TM6 | LIFVIMAVFFIFWTPYNVAILDDDC | 29 |
| TM7 | CDDDVMLVTEVIAYSHCCMNPVIYAFV | 30 |

Ac, acetylation.

To determine the effects of these peptides on CCR3-mediated chemotaxis, 4DE4-CCR3 cells were allowed to migrate to eotaxin/CCL11 in the presence of each peptide. 4DE4-CCR3, a mouse pre-B cell lymphoma line engineered to stably express human CCR3, has been used extensively to study CCR3 expression and CCR3-mediated chemotaxis. The linear transmembrane domain peptides exhibited differing levels of cytotoxicity and potency in inhibiting chemotaxis (FIG. 10). In particular, peptides corresponding to TM5, TM6, and TM7 were highly cytotoxic at all concentrations tested. Among the remaining transmembrane domain peptides, the TM1 peptide was moderately cytotoxic and TM3 and TM4 peptides showed no significant CCR3 antagonism. By comparison, TM2 demonstrated the ability to inhibit 4DE4-CCR3 cell chemotaxis toward an eotaxin gradient in a dose-dependent manner with undetectable or low cytotoxicity (FIG. 10).

What is claimed is:

1. A method or of treating or ameliorating one or more symptoms of asthma, eosinophilic esophagitis, eosinophilic colitis, allergic rhinitis, atopic dermatitis, Crohn's disease, inflammatory bowel disease, or age-related macular degeneration in a subject in need thereof, wherein the method comprises administering to the subject an effective amount of a pharmaceutical composition comprising a C-C chemokine receptor 3 (CCR3) peptide analog comprising the amino acid sequence LLNLAISDLLFLVTLPFWIHY (SEQ ID NO:17) or LLFLVTLPFWIHYVRGHNWVFGH (SEQ ID NO:18), wherein said peptide analog is (i) PEGylated, (ii) up to 50 amino acid residues in length, and (iii) optionally in the form of a nanoparticle or in admixture with a pharmaceutically acceptable carrier, thereby treating or ameliorating one or more symptoms of the subject's asthma, eosinophilic esophagitis, eosinophilic colitis, allergic rhinitis, atopic dermatitis, Crohn's disease, inflammatory bowel disease, or age-related macular degeneration.

2. The method of claim 1, wherein the pharmaceutical composition is administered to the lungs of the subject.

3. The method of claim 2, wherein said administration is via nebulization to the lungs.

* * * * *

SEQUENCE LISTING

```
<160> NUMBER OF SEQ ID NOS: 30

<210> SEQ ID NO 1
<211> LENGTH: 25
<212> TYPE: PRT
<213> ORGANISM: Artificial Sequence
<220> FEATURE:
<223> OTHER INFORMATION: Synthetic peptide

<400> SEQUENCE: 1

Leu Leu Phe Leu Val Thr Leu Pro Phe Trp Ile His Tyr Val Arg Gly
1               5                   10                  15

His Asn Trp Val Phe Gly Asp Asp Asp
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic peptide

<400> SEQUENCE: 2

Phe Gly Val Ile Thr Ser Ile Val Thr Trp Gly Leu Ala Val Leu Ala
1               5                   10                  15

Ala Leu Pro Glu Phe Ile Phe Tyr Glu Thr Glu Asp
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa denotes Thr or Ile

<400> SEQUENCE: 3

Ile Phe Val Xaa Met Ala Val Phe Phe Ile Phe Trp Thr Pro Tyr Asn
1               5                   10                  15

Val Ala Ile Leu Leu Ser Ser Tyr Gln Ser Asp Asp
            20                  25

<210> SEQ ID NO 4
```

```
<211> LENGTH: 26
<212> TYPE: PRT
<213> ORGANISM: Artificial Sequence
<220> FEATURE:
<223> OTHER INFORMATION: Synthetic peptide

<400> SEQUENCE: 4

Asp Asp Leu Val Met Leu Val Thr Glu Val Ile Ala Tyr Ser His Cys
1               5                   10                  15

Cys Met Asn Pro Val Ile Tyr Ala Phe Val
            20                  25

<210> SEQ ID NO 5
<211> LENGTH: 31
<212> TYPE: PRT
<213> ORGANISM: Artificial Sequence
<220> FEATURE:
<223> OTHER INFORMATION: Synthetic peptide

<400> SEQUENCE: 5

Leu Leu Asn Leu Ala Ile Ser Asp Leu Leu Phe Leu Val Thr Leu Pro
1               5                   10                  15

Phe Trp Ile His Tyr Val Arg Gly His Asn Trp Val Phe Gly His
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic peptide

<400> SEQUENCE: 6

Leu Leu Asn Leu Ala Ile Ser Asp Leu Leu Phe Leu Phe Thr Leu Pro
1               5                   10                  15

Phe Trp Ile His Tyr Val Arg Gly His Asn Trp Val Phe Gly His
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic peptide

<400> SEQUENCE: 7

Leu Leu Asn Leu Ala Ile Ser Asp Leu Leu Phe Leu Phe Thr Leu Pro
1               5                   10                  15

Phe Trp Ile His Tyr Val Arg Glu Arg Asn Trp Val Phe Ser His
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic peptide

<400> SEQUENCE: 8

Leu Leu Asn Leu Ala Ile Ser Asp Leu Leu Phe Leu Phe Thr Leu Val
1               5                   10                  15

Phe Trp Ile His Tyr Thr Gly Trp Asn Asp Trp Val Phe Gly Arg
            20                  25                  30
```

```
<210> SEQ ID NO 9
<211> LENGTH: 31
<212> TYPE: PRT
<213> ORGANISM: Artificial Sequence
<220> FEATURE:
<223> OTHER INFORMATION: Synthetic peptide

<400> SEQUENCE: 9

Leu Leu Asn Leu Ala Ile Ser Asp Val Leu Phe Leu Phe Thr Leu Pro
1               5                   10                  15

Phe Trp Ile His Tyr Val Arg Trp Asn Glu Trp Val Phe Gly His
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic peptide

<400> SEQUENCE: 10

Leu Phe Asn Leu Ala Ile Ser Asp Leu Leu Phe Leu Phe Thr Val Pro
1               5                   10                  15

Phe Trp Ile His Tyr Val Leu Trp Asn Glu Trp Gly Phe Gly His
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide

<400> SEQUENCE: 11

Leu Leu Asn Leu Ala Ile Ser Asp Leu Leu Phe Leu Phe Thr Val Pro
1               5                   10                  15

Phe Trp Ile His Tyr Val Leu Trp Asn Glu Trp Gly Phe Gly His
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic peptide

<400> SEQUENCE: 12

Leu Phe Asn Leu Ala Ile Ser Asp Leu Leu Phe Leu Phe Thr Leu Pro
1               5                   10                  15

Phe Trp Ile His Tyr Ile Leu Arg Lys Glu Trp Gly Phe Gly His
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic peptide

<400> SEQUENCE: 13

Leu Phe Asn Leu Ala Ile Ser Asp Leu Leu Phe Leu Phe Thr Leu Pro
1               5                   10                  15

Phe Trp Ile His Tyr Val Arg Trp Asn Glu Trp Val Phe Asp Ser
            20                  25                  30
```

```
<210> SEQ ID NO 14
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes Leu or Phe
<220> FEATURE:
<221> NAME/KEY: MISC_FEATURE
<222> LOCATION: (9)..(9)
<223> OTHER INFORMATION: Xaa denotes Leu or Val
<220> FEATURE:
<221> NAME/KEY: MISC_FEATURE
<222> LOCATION: (13)..(13)
<223> OTHER INFORMATION: Xaa denotes Phe or Val
<220> FEATURE:
<221> NAME/KEY: MISC_FEATURE
<222> LOCATION: (15)..(15)
<223> OTHER INFORMATION: Xaa denotes Leu or Val
<220> FEATURE:
<221> NAME/KEY: MISC_FEATURE
<222> LOCATION: (16)..(16)
<223> OTHER INFORMATION: Xaa denotes Pro or Val
<220> FEATURE:
<221> NAME/KEY: MISC_FEATURE
<222> LOCATION: (22)..(22)
<223> OTHER INFORMATION: Xaa denotes Ile, Thr or Val
<220> FEATURE:
<221> NAME/KEY: MISC_FEATURE
<222> LOCATION: (23)..(23)
<223> OTHER INFORMATION: Xaa denotes Arg, Gly or Leu
<220> FEATURE:
<221> NAME/KEY: MISC_FEATURE
<222> LOCATION: (24)..(24)
<223> OTHER INFORMATION: Xaa denotes Trp, Gly, Glu or Arg
<220> FEATURE:
<221> NAME/KEY: MISC_FEATURE
<222> LOCATION: (25)..(25)
<223> OTHER INFORMATION: Xaa denotes His, Arg, Asn or Lys
<220> FEATURE:
<221> NAME/KEY: MISC_FEATURE
<222> LOCATION: (26)..(26)
<223> OTHER INFORMATION: Xaa denotes Asn, Asp or Glu
<220> FEATURE:
<221> NAME/KEY: MISC_FEATURE
<222> LOCATION: (28)..(28)
<223> OTHER INFORMATION: Xaa denotes Val or Gly
<220> FEATURE:
<221> NAME/KEY: MISC_FEATURE
<222> LOCATION: (30)..(30)
<223> OTHER INFORMATION: Xaa denotes Gly, Ser or Asp
<220> FEATURE:
<221> NAME/KEY: MISC_FEATURE
<222> LOCATION: (31)..(31)
<223> OTHER INFORMATION: Xaa denotes His, Arg or Ser

<400> SEQUENCE: 14

Leu Xaa Asn Leu Ala Ile Ser Asp Xaa Leu Phe Leu Xaa Thr Xaa Xaa
1               5                   10                  15

Phe Trp Ile His Tyr Xaa Xaa Xaa Xaa Xaa Trp Xaa Phe Xaa Xaa
            20                  25                  30

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Leu or Val
```

```
<220> FEATURE:
<221> NAME/KEY: MISC_FEATURE
<222> LOCATION: (5)..(5)
<223> OTHER INFORMATION: Xaa denotes Phe or Val
<220> FEATURE:
<221> NAME/KEY: MISC_FEATURE
<222> LOCATION: (7)..(7)
<223> OTHER INFORMATION: Xaa denotes Leu or Val
<220> FEATURE:
<221> NAME/KEY: MISC_FEATURE
<222> LOCATION: (8)..(8)
<223> OTHER INFORMATION: Xaa denotes Pro or Val

<400> SEQUENCE: 15

Xaa Leu Phe Leu Xaa Thr Xaa Xaa Phe Trp Ile His Tyr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide

<400> SEQUENCE: 16

Leu Leu Phe Leu Val Thr Leu Pro Phe Trp Ile His Tyr
1               5                   10

<210> SEQ ID NO 17
<211> LENGTH: 21
<212> TYPE: PRT
<213> ORGANISM: Artificial Sequence
<220> FEATURE:
<223> OTHER INFORMATION: Synthetic peptide

<400> SEQUENCE: 17

Leu Leu Asn Leu Ala Ile Ser Asp Leu Leu Phe Leu Val Thr Leu Pro
1               5                   10                  15

Phe Trp Ile His Tyr
            20

<210> SEQ ID NO 18
<211> LENGTH: 23
<212> TYPE: PRT
<213> ORGANISM: Artificial Sequence
<220> FEATURE:
<223> OTHER INFORMATION: Synthetic peptide

<400> SEQUENCE: 18

Leu Leu Phe Leu Val Thr Leu Pro Phe Trp Ile His Tyr Val Arg Gly
1               5                   10                  15

His Asn Trp Val Phe Gly His
            20

<210> SEQ ID NO 19
<211> LENGTH: 25
<212> TYPE: PRT
<213> ORGANISM: Artificial Sequence
<220> FEATURE:
<223> OTHER INFORMATION: Synthetic peptide

<400> SEQUENCE: 19

Leu Leu Asn Leu Ala Ile Ser Asp Leu Leu Phe Leu Val Thr Leu Pro
1               5                   10                  15

Phe Trp Ile His Tyr Asp Asp Asp Cys
            20                  25
```

```
<210> SEQ ID NO 20
<211> LENGTH: 26
<212> TYPE: PRT
<213> ORGANISM: Artificial Sequence
<220> FEATURE:
<223> OTHER INFORMATION: Synthetic peptide

<400> SEQUENCE: 20

Leu Leu Phe Leu Val Thr Leu Pro Phe Trp Ile His Tyr Val Arg Gly
1               5                   10                  15

His Asn Trp Val Phe Gly His Asp Asp Asp
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (26)..(26)
<223> OTHER INFORMATION: PEGylation and amidation.

<400> SEQUENCE: 21

Leu Leu Phe Leu Val Thr Leu Pro Phe Trp Ile His Tyr Val Arg Gly
1               5                   10                  15

His Asn Trp Val Phe Gly His Asp Asp Asp
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetic peptide

<400> SEQUENCE: 22

Leu Leu Phe Leu Val Thr Leu Pro Phe Trp Ile His Tyr Val Arg Gly
1               5                   10                  15

His Asn Trp Val Phe Gly His Asp Asp Asp Cys
            20                  25

<210> SEQ ID NO 23
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (24)..(24)
<223> OTHER INFORMATION: PEGylation and amidation

<400> SEQUENCE: 23

Leu Leu Asn Leu Ala Ile Ser Asp Leu Leu Phe Leu Val Thr Leu Pro
1               5                   10                  15

Phe Trp Ile His Tyr Asp Asp Asp
            20

<210> SEQ ID NO 24
<211> LENGTH: 26
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (26)..(26)
<223> OTHER INFORMATION: PEGylation and amidation.

<400> SEQUENCE: 24

Tyr Leu Phe Leu Leu Val Thr Val Phe His Ile Trp Leu Pro His Asn
1               5                   10                  15

Arg Gly His Val Trp Gly Phe Asp Asp Asp
            20                  25

<210> SEQ ID NO 25
<211> LENGTH: 30
<212> TYPE: PRT
<213> ORGANISM: Artificial Sequence
<220> FEATURE:
<223> OTHER INFORMATION: Synthetice peptide.
<220> FEATURE:
<221> NAME/KEY: MOD_RES
<222> LOCATION: (1)..(1)
<223> OTHER INFORMATION: ACETYLATION

<400> SEQUENCE: 25

Lys Asp Asp Asp Gln Phe Val Pro Pro Leu Tyr Ser Leu Val Phe Thr
1               5                   10                  15

Val Gly Leu Leu Gly Asn Val Val Val Met Ile Leu Ile
            20                  25                  30

<210> SEQ ID NO 26
<211> LENGTH: 26
<212> TYPE: PRT
<213> ORGANISM: Artificial Sequence
<220> FEATURE:
<223> OTHER INFORMATION: Synthetic peptide.
<220> FEATURE:
<221> NAME/KEY: MOD_RES
<222> LOCATION: (1)..(1)
<223> OTHER INFORMATION: ACETYLATION

<400> SEQUENCE: 26

Lys Asp Asp Asp Leu Leu Ser Gly Phe Tyr His Thr Gly Leu Tyr Ser
1               5                   10                  15

Glu Ile Phe Phe Ile Ile Leu Leu Thr Ile
            20                  25

<210> SEQ ID NO 27
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION

<400> SEQUENCE: 27

Val Thr Phe Gly Val Ile Thr Ser Ile Val Thr Trp Gly Leu Ala Val
1               5                   10                  15

Leu Ala Ala Leu Pro Glu Phe Ile Phe Asp Asp Asp Lys
            20                  25

<210> SEQ ID NO 28
<211> LENGTH: 24
<212> TYPE: PRT
<213> ORGANISM: Artificial sequence
<220> FEATURE:
```

```
<223> OTHER INFORMATION: Synthetic peptide

<400> SEQUENCE: 28

Cys Asp Asp Thr Ile Phe Cys Leu Val Leu Pro Leu Leu Val Met
1               5                   10                  15

Ala Ile Cys Tyr Thr Gly Ile Ile
            20

<210> SEQ ID NO 29
<211> LENGTH: 25
<212> TYPE: PRT
<213> ORGANISM: Artificial sequence
<220> FEATURE:
<223> OTHER INFORMATION: Synthetic peptide

<400> SEQUENCE: 29

Leu Ile Phe Val Ile Met Ala Val Phe Phe Ile Phe Trp Thr Pro Tyr
1               5                   10                  15

Asn Val Ala Ile Leu Asp Asp Asp Cys
            20                  25

<210> SEQ ID NO 30
<211> LENGTH: 27
<212> TYPE: PRT
<213> ORGANISM: Artificial sequence
<220> FEATURE:
<223> OTHER INFORMATION: Synthetic peptide

<400> SEQUENCE: 30

Cys Asp Asp Val Met Leu Val Thr Glu Val Ile Ala Tyr Ser His
1               5                   10                  15

Cys Cys Met Asn Pro Val Ile Tyr Ala Phe Val
            20                  25
```